United States Patent
Leddy et al.

(10) Patent No.: US 7,992,422 B2
(45) Date of Patent: Aug. 9, 2011

(54) BREATH-BASED SENSORS FOR NON-INVASIVE MOLECULAR DETECTION

(75) Inventors: Johna Leddy, Iowa City, IA (US); Luke M. Haverhals, Coralville, IA (US)

(73) Assignee: University of Iowa Research Foundation, Iowa City, IA (US)

(*) Notice: Subject to any disclaimer, the term of this patent is extended or adjusted under 35 U.S.C. 154(b) by 260 days.

(21) Appl. No.: 12/192,038

(22) Filed: Aug. 14, 2008

(65) Prior Publication Data

US 2008/0295573 A1 Dec. 4, 2008

Related U.S. Application Data

(62) Division of application No. 11/305,799, filed on Dec. 16, 2005, now Pat. No. 7,421,882.

(60) Provisional application No. 60/636,951, filed on Dec. 17, 2004.

(51) Int. Cl.
*G01N 1/22* (2006.01)

(52) U.S. Cl. ............ 73/23.3; 422/84; 436/900; 600/529; 600/532; 600/543

(58) Field of Classification Search .............. 73/23.3; 422/84; 436/106, 116–118, 128, 900; 600/529, 600/532, 543
See application file for complete search history.

(56) References Cited

U.S. PATENT DOCUMENTS

| | | |
|---|---|---|
| 3,966,579 A | 6/1976 | Chang et al. |
| 4,487,055 A | 12/1984 | Wolf |
| 4,749,553 A * | 6/1988 | Lopez et al. ............ 422/84 |
| 4,770,026 A | 9/1988 | Wolf |
| 4,926,164 A | 5/1990 | Porter et al. |
| 5,048,321 A | 9/1991 | Chow |

(Continued)

FOREIGN PATENT DOCUMENTS

WO  WO 92/22813  12/1992

(Continued)

OTHER PUBLICATIONS

Freudernrich, How Breathalyzers Work, www.howstuffworks.com, 1998-2007, 4 pages.

(Continued)

*Primary Examiner* — Daniel S Larkin
(74) *Attorney, Agent, or Firm* — Foley & Lardner LLP

(57) ABSTRACT

A method of diagnosing the health of an individual by collecting a breath sample from the individual and measuring the amount of each of a plurality of analytes in the sample. The amount of each analytes is measured by fitting a time response curve of a sample-evaluation fuel cell in which the fuel cell sample electrode is contacted with the sample with the analysis based on a function of standard time response curves for an equivalent fuel cell configuration obtained separately for each of the analytes on a fuel cell with equivalent construction as sample-evaluation fuel cell. Each of the plurality of analytes is generally indicative of an aspect of the individual's health. Suitable analytes include, for example, inorganic compounds as well as compositions that exhibit negative reduction reactions at least for a portion of the time response curve. In particular, acetone exhibits a negative potential/current peak when it is an analyte in a fuel cell in an sample electrode with a counter electrode exposed to oxygen, which may or may not be introduced in the form of air. Various forms of analysis to estimate acetone concentrations in the breath can be used.

12 Claims, 12 Drawing Sheets

U.S. PATENT DOCUMENTS

| | | | |
|---|---|---|---|
| 5,081,871 A | 1/1992 | Glaser | |
| 5,132,193 A | 7/1992 | Reddy et al. | |
| 5,291,898 A | 3/1994 | Wolf | |
| 5,302,471 A | 4/1994 | Ito et al. | |
| 5,426,415 A | 6/1995 | Prachar et al. | |
| 5,458,853 A | 10/1995 | Porter et al. | |
| 5,595,832 A | 1/1997 | Tomimatsu et al. | |
| 5,595,833 A | 1/1997 | Gardner et al. | |
| 5,753,185 A | 5/1998 | Mathews et al. | |
| 5,928,804 A | 7/1999 | Leddy et al. | |
| 6,479,176 B2 | 11/2002 | Leddy et al. | |
| 6,795,775 B2 | 9/2004 | Traylor, III | |
| 7,014,612 B2 * | 3/2006 | Hubbard et al. | 600/532 |
| 7,364,551 B2 * | 4/2008 | Allen et al. | 600/532 |
| 2002/0084130 A1 | 7/2002 | Der Ghazarian et al. | |
| 2002/0177232 A1 | 11/2002 | Melker et al. | |
| 2002/0198574 A1 | 12/2002 | Gumpert | |
| 2003/0004426 A1 | 1/2003 | Melker et al. | |
| 2003/0117287 A1 | 6/2003 | Crespo | |
| 2003/0121309 A1 | 7/2003 | Fikus et al. | |
| 2003/0183427 A1 | 10/2003 | Tojo et al. | |
| 2003/0208133 A1 | 11/2003 | Mault | |
| 2004/0137637 A1 | 7/2004 | Wang et al. | |
| 2005/0084921 A1 | 4/2005 | Cranley et al. | |
| 2005/0214169 A1 | 9/2005 | Leddy et al. | |
| 2006/0130557 A1 | 6/2006 | Leddy et al. | |

FOREIGN PATENT DOCUMENTS

| | | |
|---|---|---|
| WO | WO 93/05393 | 3/1993 |

OTHER PUBLICATIONS

Alcohol and the Human Body, Intoximeters, Inc., 1995-2007, 6 pages.

Harris et al., Self Monitoring of Blood Glucose by Adults With Diabetes in the United States, Diabetes Care, Aug. 1993, vol. 16, No. 8, pp. 116-1123, 8 pages.

Tassopoulos et al., Breath-Acetone and Blood-Sugar Measurements in Diabetes, The Lancet, Jun. 28, 1969, vol. 1, pp. 1281-1286, 5 pages.

Kim et al., "Detection of ethanol gas concentration by fuel cell sensors fabricated using a solid polymer electrolyte," Sensors and Actuators, 2000, pp. 194-198, vol. B 67.

Fenske et al., "Human Breath Emissions of VOCs," J. Air & Waste Manage. Assoc., May 1999, pp. 594-598, vol. 49.

Glover, "Toluene and the Intoxilyzer 5000®: No Response To Concentrations Found On Human Breath," International Conference on Alcohol, Drugs, and Traffic Safety, (May 22-26, 2000).

Jones, "Fifty Years on—Looking Back at Developments in Methods of Blood-and Breath-Alcohol Analysis," International Conference on Alcohol, Drugs and Traffic Safety, May 22-26, 2000.

Manolis, "The Diagnostic Potential of Breath Analysis," Clin. Chem., 1983, pp. 5-15, vol. 29, No. 1.

Millet et al., "A solid polymer electrolyte-based ethanol gas sensor," J. Applied Electrochem., 1996, pp. 933-937, vol. 26.

Paulsson et al., "Analysis of breath alcohol with a multisensor array: instrumental setup, characterization and evaluation," Forensic Science International, 1999, pp. 95-114, vol. 105.

Sanchez et al., "GC Analysis of Human Breath with a Series-Coupled Column Ensemble and a Multibed Sorption Trap," Anal. Chem., May 15, 2003, pp. 2231-2236, vol. 75.

Verstraete, "Perspectives for the detection of cannabis in breath," International Conference on Alcohol, Drugs and Traffic Safety, May 22-26, 2000, pp. 1-5.

Musa-Veloso et al., "Breath Acetone is a Reliable Indicator of Ketosis in Adults Consuming Ketogenic Meals," American Journal of Clinical Nutrition, 2002, pp. 65-70, vol. 76.

Likhodii et al., "Breath Acetone as a Measure of Systemic Ketosis Assessed in a Rat Model of the Ketogenic Diet," Clinical Chemistry, 2002, pp. 115-120, vol. 48.

Fleischer et al., "Detection of Volatile Compounds Correlated to Human Diseases through Breath Analysis with Chemical Sensors," Sensors and Actuators B, 2002, pp. 245-249, vol. 83.

Musa-Veloso et al., "Epilepsy and the Ketogenic Diet: Assessment of Ketosis in Children Using Breath Acetone," Pediatric Research, 2002, pp. 443-448, vol. 52.

Phillips et al., "Variation in Volatile Organic Compounds in the Breath of Normal Humans," J. Chromatography B, 1999, pp. 75-88, vol. 729.

Phillips, "Method for the Collection and Assay of Volatile Organic Compounds in Breath," Analytical Biochemistry, 1997, pp. 272-278, vol. 247.

Yu et al., "Analysis of Diabetic Patient's Breathe Using Conducting Polymer Sensor Array," Chemical Sensors (2005), 305-308.

Philips, "Detection of carbon disulfide in breath and air: a possible new risk factor for coronary artery disease," International Archives of Occupational and Environmental Health, 1992, pp. 119-123, vol. 64.

Philips et al., "Volatile Organic Compounds In Breath As Markers of Lung Cancer: A Cross-Sectional Study," Lancet, 1999, pp. 1930-1933, vol. 353.

Zhang et al., "Diagnosis of Diabetes by Image Detection of Breath using Gas-Sensitive Laps," Biosensors & Bioelectronics, 2000, pp. 249-256, vol. 15.

Wang et al., "Blood Acetone Concentration in 'Normal People' and in exposed workers 16 h after the end of the workshift," International Achieves of Occupational and Environmental Health, 1994, pp. 285-289, vol. 65.

Kalapos, "On the Mammalian Acetone Metabolism: From Chemistry to Clinical Implications," Biochimica et Biophysica Acta, 2003, pp. 122-139, vol. 1621.

Diskin et al., "Increase of Acetone and Ammonia in Urine Headspace and Breath During Ovulation Quantified using Selected Ion Flow Tube Mass Spectrometry," Institute of Physics Publishing; Physiol. Meas., 2003, pp. 191-199, vol. 23.

Goschke et al., "Aceton in der Atemluft und Ketone im Venenblut bei vollständigem Fasten normal-und übergewichtiger Personen," Res. Exp. Med., 1975, pp. 233-244, vol. 165.

Sacks et al., "Guidelines and Recommendations for Laboratory Analysis in the Diagnosis and Management of Diabetes Mellitus," Chemical Chemistry, 2002, pp. 436-472, 48:3.

Laffel, "Ketone Bodies: A Review of Physiology, Pathophysiology and Application of Monitoring to Diabetes," Diabetes/Metabolism Research and Reviews, 1999, pp. 412-426, vol. 15.

* cited by examiner

BREATH-BASED SENSORS FOR NON-INVASIVE MOLECULAR DETECTION

CROSS REFERENCE TO RELATED APPLICATIONS

This application is a division of U.S. application Ser. No. 11/305,799 filed Dec. 16, 2005, now U.S. Pat. No. 7,421,882, which claims priority to U.S. provisional application 60/636, 951 filed on Dec. 17, 2004 to Leddy et al., both incorporated herein by reference in their entireties.

FIELD OF THE INVENTION

The present invention relates to approaches for measuring and differentiating volatile organic and/or inorganic compositions in vapor samples. More particularly, the present invention relates to using fuel cells as sensors for measuring the amount of various diagnostic analytes, which can be characteristic of a disease state, in an individual's breath.

BACKGROUND OF THE INVENTION

Acetone found in a human's blood, urine, and breath can be a marker for various biological processes, the most notable of which is diabetic ketoacidosis associated with insulin insufficiency. Also, acetone can also be an indicator of poor regulation of a ketogenic diet that is used to control refractory epileptic seizures.

Conventional monitoring devices for diabetic ketoacidosis and regulating ketogenic diets often rely on invasive sample collection, such as blood tests. The American Diabetes Association recommends that diabetics monitor their glucose levels several times a day. However, because of the invasive nature of conventional monitoring devices, many diabetics with type 1 ("insulin dependent") diabetes monitor glucose levels only once a day and most diabetics with type 2 ("insulin resistant") diabetes do not monitor glucose levels daily.

Ketone generation in the body is known to be associated with certain conditions. Referring to FIG. 1, insulin facilitates the transport of glucose into the cell to generate energy. Diabetes generally occurs when either the amount of insulin is insufficient (type 1 diabetes) or the insulin is not effective (type 2 diabetes). As a result, the blood glucose level can rise and the cells become glucose-starved. Ketogenesis in the mitochondria then converts triglycerides (fatty acids) to acetoacetate (AcAc) and energy. The AcAc interconverts with 3-hydroxybutyrate (3HB) and also undergoes spontaneous decarboxylation to form acetone ($Me_2O$). Together these three products (AcAc, 3HB, and $Me_2O$) are known as ketone bodies, which can partition across the cell wall and into the blood.

Of the three ketone bodies, only acetone is sufficiently volatile to partition into the alveolar air, while AcAc and 3HB remain in the blood. The partition coefficient, K, for $Me_2O$ at the blood/air interface is between 208 and 597, a factor even more favorable that that of ethanol. The ethanol partition coefficient is used in determining the blood alcohol content or blood alcohol concentration (BAC) of an individual. The acetone that partitions into the alveolar air generates the sweet smell characteristic of diabetic ketoacidosis, which is sometimes referred to as "acetone breath."

Diabetic ketoacidosis occurs as the fatty acids are consumed and the concentration of ketone bodies rises. For normal subjects, the concentration ratio of 3HB to AcAc is about 1:1 and the total concentration of ketone bodies is below 0.5 mM. Under diabetic ketoacidotic conditions, the ratio of 3HB to AcAc increases to about 3:1, or even as high as 10:1, and the concentration of the ketone bodies drastically increases. Concentrations for the ketone bodies are listed in Table 1 for human subjects who are healthy individuals, treated diabetics, and ketoacidotic diabetics.

TABLE 1

Plasma Concentrations of Ketone Bodies in Plasma (mM).

| Ketone Body | Normal Subject | Treated Diabetic | Ketoacidotic Diabetic |
|---|---|---|---|
| Acetone ($Me_2O$) | 0.015 ± 0.005 | 1.69 ± 0.78 | 3.26 ± 0.79 |
| Acetoacetate (AcAc) | 0.114 ± 0.029 | 0.306 ± 0.05 | 2.84 ± 0.40 |
| 3-Hydroxy-butyrate (3HB) | 0.160 ± 0.050 | 0.810 ± 0.171 | 8.23 ± 1.48 |
| pH | — | — | 7.29 ± 0.01 |

As can be seen in Table 1, the concentration of acetone in a ketoacidotic diabetic is approximately two times greater than that of a treated diabetic, and the concentration of acetone is roughly a hundred times greater in a treated diabetic than a normal subject. Also, the concentrations of AcAc and 3HB in a ketoacidotic diabetic are roughly 25 times higher and 50 times higher than that of a normal subject, respectively.

The ketone body composition illustrates that acetone measurement can be an effective marker for the onset of ketoacidosis and the ketoacidotic state. Ketoacidosis can be followed by the 3HB concentration as it tracks with the total ketone load. Breath acetone correlates with plasma 3HB over a clinically relevant range. Thus, by tracking acetone on the breath, 3HB can be reliably measured and the onset of ketoacidosis can be tracked.

Portable sensors have been developed for measuring alcohol on a human's breath. Breathalyzers determine the BAC by measuring the ethanol concentration in alveolar air that is exhaled from deep within the lungs. Because there is an equilibrium of ethanol between the blood and alveolar air, the ethanol concentration in the breath is generally proportional to the ethanol concentration in the blood.

SUMMARY OF THE INVENTION

In all of the following, the potential/current time response curve is discussed with respect to a sample analyte being exposed to a fuel cell sample electrode and a selected reactant exposed to the counter electrode. In principle, the electronics for making the measurement can be connected with either polarity, although only one connection results in the conventional response curve. To simplify the discussion, the following is based on a conventional connection for measuring the response curve with a positive displacement corresponding to oxidation at the sample electrode and reduction at the counter electrode. If the alternative connection is made, all of the values can be reversed in sign to use the analysis below, although alternatively the sign can be changed and notations correspondingly flipped in the following analyses.

In a first aspect, the invention pertains to a method for the estimation of acetone concentration in a person's breath. Generally, the method comprises fitting a time response curve of a sample-evaluation fuel cell in which a sample electrode of the fuel cell is exposed to a breath sample and a counter electrode of the fuel cell is exposed to $O_2$. The fitting can be performed through the de-convolution of the sample time response curve in comparison of the sample time response curve with the time response curve of standard aqueous acetone solutions. This method can be adapted for the evaluation of diabetic ketoacidosis of an individual by estimating the concentration of acetone in a person's blood stream from an estimate of acetone concentration within the breath sample.

In further aspects, the invention pertains to a method for diagnosing the health of an individual in which the method comprises measuring the amount of a plurality of analytes in a breath sample from an individual. The measurements are obtained through fitting a time response curve of a sample-evaluation fuel cell. In some embodiments, at least one of the analytes has a negative potential peak in the time response curve indicating a reduction process. A sample electrode of the fuel cell is exposed to a breath sample, and the counter electrode of the fuel cell is exposed to a selected reactant. The selected reactant can comprise $O_2$, which may or may not be delivered as air.

In other aspects, the invention pertains to a method for diagnosing the health of an individual in which the method comprises measuring the amount of a plurality of analytes in a breath sample from an individual. The measurements are obtained through fitting a time response curve of a sample-evaluation fuel cell. In some embodiments, at least one of the analytes is an inorganic compound. A sample electrode of the fuel cell is exposed to a breath sample, and the counter electrode of the fuel cell is exposed to a selected reactant. The selected reactant can comprise $O_2$, which may or may not be delivered as air.

Moreover, the invention pertains to a system comprising a flow apparatus, a fuel cell and an analyzer. The flow apparatus is configured to operably receive a breath sample from an individual. The fuel cell comprises a sample electrode operably coupled to the flow apparatus and a counter electrode exposed to $O_2$. The sample transported within the flow system operably contacts the sample electrode. The analyzer receives a signal related to the potential of the fuel cell and evaluates the amount of acetone from a time response of the fuel cell signal as a function of time based on a standard time response of the fuel cell with acetone.

DETAILED DESCRIPTION OF THE PREFERRED EMBODIMENTS

Figure 1:
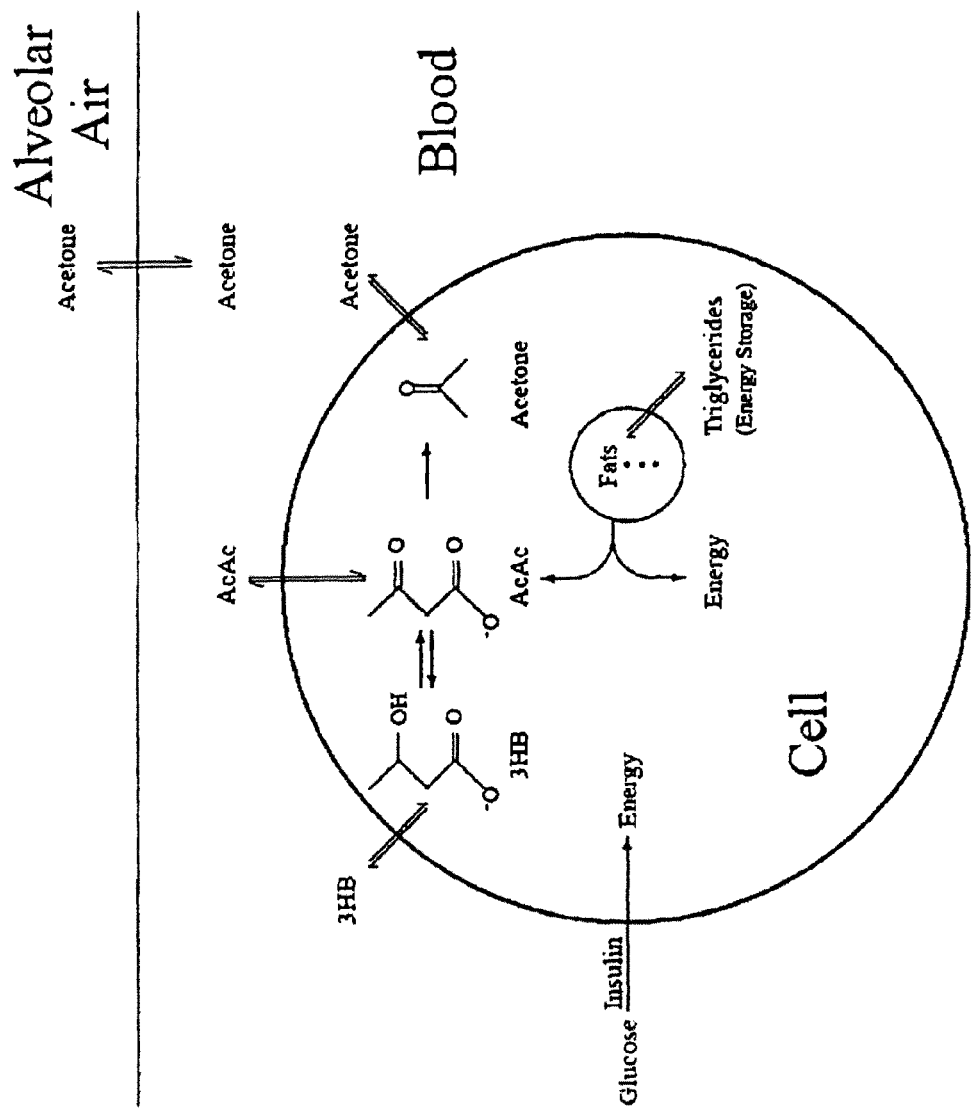
FIG. 1 is a schematic representation of fatty acid metabolism.

A vapor analysis system comprising a breath-based sensor can be used for noninvasive detection of acetone and other analytes in a human's breath. The analysis of these analytes in the breath can be used for diagnostic purposes and/or for the evaluation of a particular condition to which the person is known to be susceptible. For example, acetone is a marker for various biological processes, the most notable of which is diabetic ketoacidosis that is associated with insulin insufficiency and poor regulation of the ketogenic diet used to control refractory epileptic seizures. The breath-based sensor, which can be portable, according to the various embodiments provides a highly selective, non-invasive, and rapid measurement device having the accuracy, precision, and detection limit appropriate to the assay of acetone in the physiologically relevant range for these conditions. Other compounds characteristic of various disease states can also be measured by the breath-based sensor as described herein. Representative compounds include, for example, carbonyl sulfide (COS) as a marker for lung transplant rejection, ammonia ($NH_3$) in end stage renal failure, carbon disulfide ($CS_2$) as a marker for coronary artery disease, alkanes and benzene derivatives in the breath of lung cancer patients, and nitric oxide (NO) as a marker for asthma. Thus, the techniques herein extend to volatile inorganic analytes in a person's breath. Also, the sample evaluations are shown to extend to analytes, such as acetone, that undergo a reduction reaction at the sample electrode, at least over a portion of the time response curve, against a counter electrode exposed to a suitable reactant, such as oxygen, i.e., $O_2$.

The signature of the time response curve for a fuel cell signal, e.g., voltage/potential or current, upon exposure with volatile organic compositions from a breath sample can be used to evaluate the relative concentrations of a combination of compositions in the sample. Corresponding systems can be designed to collect a vapor sample that contains volatile compositions and direct the sample to the sample electrode of a fuel cell. The fuel cell response as a function of time is a signature for a particular compound. For samples that have a plurality of volatile organic compositions, the fuel cell response is for practical purposes a linear or nonlinear combination of the response of the fuel cell for the particular compositions appropriately weighed for the relative amounts. Therefore, an analysis can be performed to de-convolute the time response curve to obtain values for the relative concentrations. Average standard curves can be used for the performance of the de-convolution. For samples such as acetone with a distinctive negative reduction peak in the time response curve, fitting of the area, the depth of the peak or the general time response curve shape can be used to estimate concentrations of acetone or other reducing analytes. In some embodiments, the vapor sample is a breath sample from a person, or other patient, such as a pet or farm animal for medical evaluation.

Generally, a volatile organic composition evaluation system comprises a vapor/gas sampling component, a flow apparatus, a fuel cell and an analysis instrument. Vapor refers generally to gas(es) and/or vapor of a volatile composition(s) at a particular vapor pressure. The sampling component comprises an appropriate collection system suitable for the particular application of the system. For a breath analyzer, the sampling component can comprise a mouthpiece and associated conduits to connect the flow with the flow apparatus. The flow apparatus directs the gas sample to a fuel cell. The fuel cell comprises a sample electrode operably connected to the flow apparatus in which the fuel cell generates a voltage or current in response to a broad range of volatile organic and/or inorganic compositions reacting at the sample electrode. The counter electrode can be exposed to a selected reactant. In some embodiments, the counter electrode can be exposed to air, although an alternative oxygen ($O_2$) source or other chemical supply can be used to supply reactant to the counter electrode. The analysis instrument measures the fuel cell output signal, e.g., voltage or current, as a function of time from the fuel cell and evaluates the composition of the vapor in response to the fuel cell performance as a function of time.

The sample electrode can function as an anode for the oxidation of the analyte while the electrode exposed to atmospheric oxygen functions as a cathode to reduce the molecular oxygen ($O_2$). However, alternatively, the sample electrode can function as a cathode with the reduction of the analyte and with the corresponding oxidation taking place at the electrode exposed to air or other reactant. In addition, the respective electrodes can function partially as both anodes and cathodes either simultaneously or sequentially with the passage of time as different analytes react within the analyzer. For example, as discussed below, acetone is reduced in the analyzer at least initially although the resulting reduced compound may be subsequently oxidized. Also, one analyte such as acetone may be reduced while another analyte, such as ethanol, may be oxidized.

Fuel cells of particular interest are proton exchange membrane fuel cells, also known as PEM fuel cells. Polymer electrolyte membrane fuel cells are one type of proton exchange membrane fuel cells. Proton exchange membrane fuel cells have a separator or electrolyte between the anode and cathode that provides for transport of protons across the separator. Generally, the separator/electrolyte is hydrated to perform its function as electrolyte. The separator can be a polymer film. PEM fuel cells operate at lower temperatures than most other fuel cell types with operating temperatures generally less than about 100° C. and can be operated at temperatures down to freezing.

Other types of fuel cells may also be appropriate, such as phosphoric acid fuel cells, molten carbonate fuel cells and solid oxide fuel cells. Phosphoric acid fuel cells use phosphoric acid as the electrolyte. These fuel cells generally operate at about 150° C. to about 220° C. The electrolyte for molten carbonate fuel cells is molten carbonate salts, as their name implies. To achieve sufficient ion mobility through the carbonate salts, these fuel cells operate at temperatures on the order of 650° C. The electrolyte for solid oxide fuel cells is a ceramic oxide material that can transport $O_2^-$ ions at temperatures from 600° C. to about 1000° C. Phosphoric acid fuel cells, molten carbonate fuel cells and solid oxide fuel cells are described, respectively, in U.S. Pat. No. 5,302,471 to Ito et al., entitled "Compact Phosphoric Acid Fuel Cell System And Operating Method Thereof," U.S. Pat. No. 5,595,832 to Tomimatsu et al., entitled "Molten Carbonate Fuel Cell," and U.S. Pat. No. 5,595,833 to Gardner et al., entitled "Solid Oxide Fuel Cell Stack," all of which are hereby incorporated by reference herein. Since PEM fuel cells are desired due to their operating temperatures and other desirable characteristics, the following discussion focuses on these embodiments, although other fuel cell types can be substituted based on the disclosure herein.

The fuel cell should have an appropriate response for a range of organic and/or inorganic analytes. While commercial fuel cells for ethanol detection may not be well suited for the present applications, they may provide acceptable performance for the present applications. PEM fuel cells generally have catalyst materials in contact with both sides of the electrolyte/separator. One side forms the electrode exposed to oxygen in the atmosphere. The other side of the electrolyte/separator forms the analyte electrode where the analyte reacts. Protons, or other available ions, typically flow from the anode to the cathode as mediated by the electrolyte.

In some embodiments, fuel cells with magnetic composites can be particularly desirable due to their improved transport of paramagnetic materials, such as oxygen to the appropriate electrode and enhance electrolysis. Fuel cells with magnetic materials incorporated into the fuel cell are described further, for example, in U.S. Pat. No. 6,479,176 to Leddy et al, entitled "Gradient Interface Magnetic Composites And Methods Therefor," and U.S. Pat. No. 5,928,804 to Leddy et al., entitled "Fuel Cells Incorporating Magnetic Composites Having Distinct Flux Properties," both of which are incorporated herein by reference.

For power production, fuel cells are generally formed into stacks with a series of fuel cells connected in series to generate an additive voltage from the cells. Bipolar plates or other suitable current collector with flow channels separate adjacent cells. However, in general, for the present application, a single fuel cell of modest size is suitable that generates a reasonable voltage or current for the particular supply of volatile analytes. Voltage is not substantially dependent on electrode area, although small changes in internal resistance may relate to electrode area. Using a single fuel cell, the structure of the systems can be much simpler in comparison with a fuel cell stack, especially with respect to the flow of analyte and counter electrode reactant, generally, oxygen from air. However, the sensor can use a plurality of fuel cells, such as two fuel cells or more than two fuel cells, connected either in parallel of in series to obtain desired responsiveness of the sensor.

The analysis is based on a unique time dependent signature of the different volatile organic and/or inorganic compositions with respect to the time dependent response of a fuel cell operating using the volatile organic composition as a reactant. To de-convolute the time dependent response curve, standard curves are generated for selected volatile reactant compounds or particular mixtures thereof, which are thought or known to be in a breath sample for analysis. The particular mixtures can be analyzed together as a particular composition. For example, tobacco smoke, such as cigarette smoke, has a mixture of volatile organic compounds that are relatively fixed with respect to relative amounts such that the mixture can be considered a separate composition that is analyzed together for the purposes of the de-convolution. The standard curves can be based on averages from a plurality of runs to improve the precision and accuracy of the standard curve. Then, the sample curve can be de-convoluted with the standard curves.

The de-convolution can be based on a linear or non-linear combination at a plurality of time points.

The methodologies described herein can be used in a variety of applications, such as breathalyzers, vehicle interlocks, medical diagnostics, screening of large populations and environmental evaluations. Fuel cells are already used commercially for breathalyzers for the detection of ethanol to determine if the values are within legal limits. Portable devices can be used by law enforcement officials for testing drivers suspected of driving under the influence of alcohol. Similarly, other devices have been connected to vehicles, especially automobiles, for the evaluation of the sobriety of a potential driver and disabling the vehicle as appropriate. These devices can benefit from the improved analytical systems and methodologies described herein since more accurate readings can be obtained if a variety of sources of volatile organic compositions can be distinguished. Present commercial fuel cell breathalyzers generally are not suitable alone for evidentiary purposes.

Furthermore, volatile compositions, e.g., organic solvents, are often environmental pollutants that result from a wide range of human activities. The ability to efficiently identify pollutants in a particular gas sample can greatly facilitate the evaluation of a potential environmental pollutant. Similar to the evaluation of environmental pollutants, analyses can be performed in industrial settings to evaluate release of pollutants and/or to evaluate exposure levels to individuals to determine if they are within acceptable levels. These industrial limits may be evaluated in view of specific regulations, such as regulations from the U.S. Occupational Health and Safety Administration (OSHA) or the U.S. Environmental Protection Agency (EPA).

In other embodiments, measurements from the systems described herein can assist with medical evaluations since the presence of certain compositions in the breath can be indicative of certain illnesses or conditions. For example, the level of acetone in a person's breath can be used to evaluate the presence of a diabetic condition or similarly to evaluate the maintenance of the person's diabetic control. As seen below, acetone has a distinctive signature in the fuel cell response curve that can be used to evaluate acetone concentration. In other embodiments, the analyzer can be used to evaluate the health of a person, who may or may not have identifiable symptoms. For example, the analysis can be performed as part of a well patient visit for the early detection of conditions such as diabetes. Alternatively, the analysis can be performed as part of a diagnosis procedure on a patient with symptoms that have not yet been definitively connected with a particular disease. For the measurement of unknown analytes for medical diagnosis, the fuel cell response curve is generally deconvoluted with respect to a range of potential analytes found in a person's breath. For samples thought to include acetone, the distinctive negative peak can be used for evaluating the concentration of acetone, and several specific algorithms are described below.

Once estimates of the concentration of medically related analytes are determined within a person's breath, these breath concentrations can be correlated with serum concentrations using either known relationships or relationships that can be determined through measurements on individuals within known medical conditions. Using the estimates of serum concentrations of various analytes, this information can be incorporated as additional data that can be used for diagnostic purposes along with other tests and examinations. Generally, a medical professional would be involved in the evaluation of the collective test information for arriving at the ultimate diagnosis.

Vapor Analysis System

A vapor analysis system generally comprises a vapor/gas sampling component, a flow apparatus, a fuel cell and an analysis instrument. The sampling component can be designed based on the source of the particular sample. In some embodiments of interest, the vapor sampling component can be a breath collection component. The flow apparatus provides for controlled flow of the vapor sample to the fuel cell. The analysis instrument collects the time dependent response of the fuel cell following interaction with the vapor sample and the de-convolution of the time dependent response of the fuel cell to obtain the relative amounts of the samples. While the fuel cell can be optimized for certain analytes such as ethanol, general fuel cells can be used that are responsive to organic compositions and/or inorganic compositions generally. Thus, a fuel cell sensor may or may not be sensitive to a particular analyte depending on the particular objective of the device.

Figure 2:
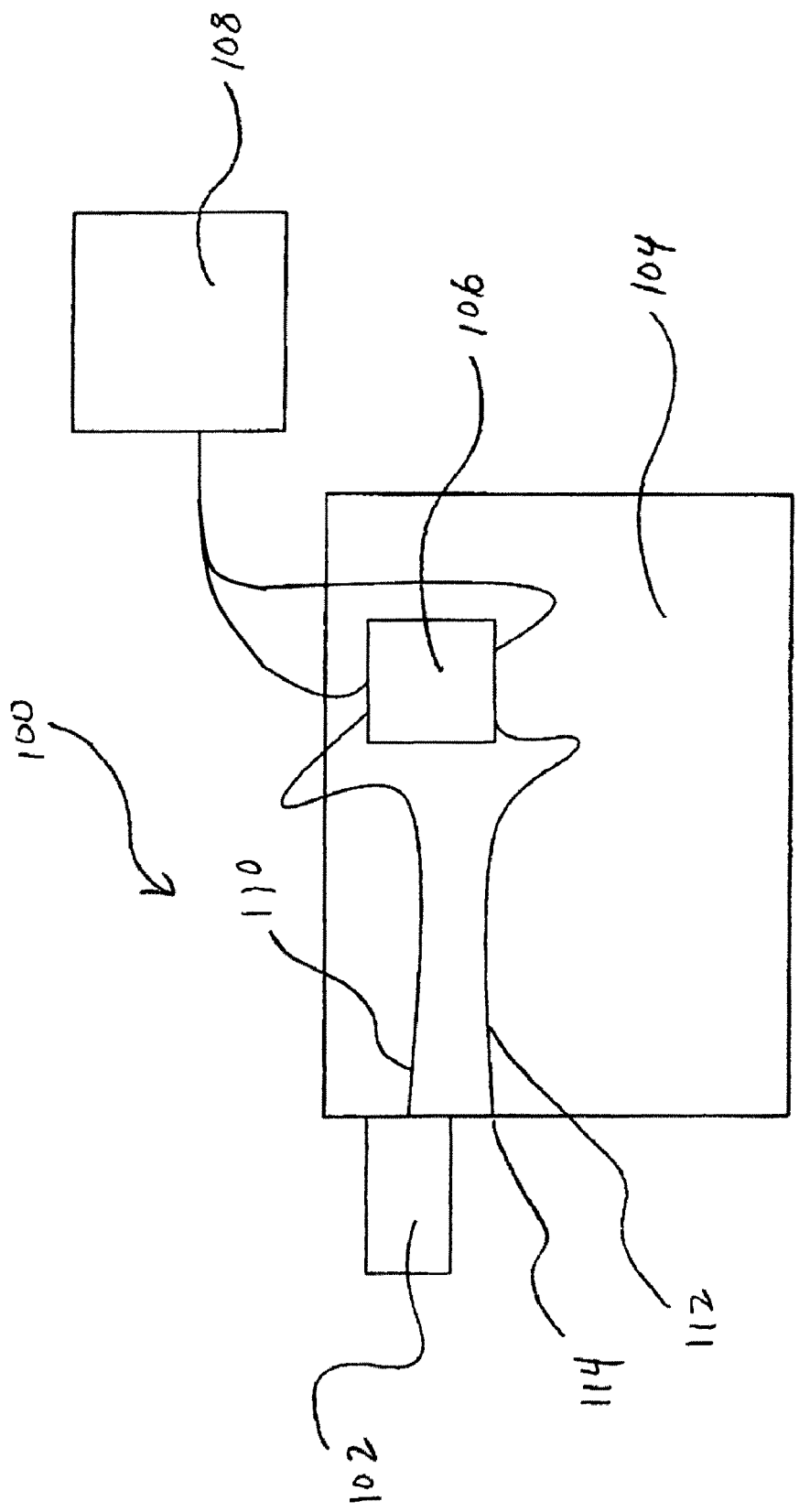
FIG. 2 is a schematic representation of a system for evaluation of amounts of volatile organic compositions in a vapor sample as described herein.

Referring to FIG. 2, a schematic diagram is depicted for a vapor analysis system described herein. A vapor analysis system 100 can comprise sampling component 102, flow apparatus 104, fuel cell 106 and analysis instrument 108. Sampling component 102 facilitates introducing a vapor sample into flow apparatus 104. In general, sampling component 102 can be any mechanical or passive structure that facilitates collection and introduction of desired vapors into the flow apparatus and/or the fuel cell of a vapor analysis system. Sampling component 102 can comprise appropriate combinations of one or more tubes, mouthpieces, or the like.

In some embodiments, flow apparatus 104 can comprise inlet flow line 110, which provides a fluid flow pathway for vapor samples from sampling component 102 to the sample electrode of fuel cell 106. Flow apparatus 104 can also comprise outlet flow line 112, which provides a vapor flow pathway for vapor samples and/or fuel cell by-products from the sample electrode of fuel cell 106 to, for example, exhaust 114. In some embodiments, flow apparatus 104 and/or fuel cell 106 can comprise one or more pumps to facilitate moving vapor samples into and out of the sample electrode of fuel cell 106. Vapor analysis system 100 can be configured to function in a variety of devices such as, for example, breathalyzers, ignition interlock systems, medical diagnostic devices, broad population screening, and environmental and industrial sensors or monitors.

As described below, the various components of vapor analysis system 100 can be adjusted and designed to suit the intended application of the device. In embodiments where the vapor analysis system is designed to be incorporated into a breathalyzer, sampling component 102 can comprise stem having a tube fitting adapted to removably engage a sample tube or mouthpiece. In some embodiments, the stem can be formed integrally with the housing of the breathalyzer. Breathalyzers having a stem and a tube fitting are described in U.S. Pat. No. 4,487,055 to Wolf, entitled "Breath Alcohol Testing Device," which is hereby incorporated by reference herein. In embodiments where the vapor analysis system is designed to be incorporated into an ignition interlock, sampling component 102 can comprise a mouthpiece that extends from the interior of the housing to the exterior of the housing. Sampling components for ignition interlocks are described in, for example, U.S. Pat. No. 5,426,415 to Prachar et al., entitled "Breath Analyzer For Use In Automobile Ignition Locking Systems," which is hereby incorporated by reference herein. In other embodiments, the vapor analysis system can be incorporated in medical diagnostic devices or an environmental sensor or detector. Suitable breath sampling components for a medical examination are described, for example, in U.S. Pat. No. 5,081,871 to Glazer, entitled "Breath Sampler," incorporated herein by reference. Suitable environmental sampling systems are described for example in U.S. Pat. No. 5,753,185 to Mathews et al., entitled "Vehicle Emissions Testing System," incorporated herein by reference.

The vapor analysis devices 100 of the present disclosure can comprise a flow apparatus 104 that provides desired fluid flow within vapor analysis device. In general, flow apparatus 104 can regulate and provide fluid flow to and from fuel cell 106 during analysis of a sample. Flow apparatus can comprise appropriate combinations of flow lines or pipes and one or more pumps to facilitate desired fluid flow within vapor analysis system 100. The pump and/or other flow control elements can be connected to a microcomputer, which can control the function of the pump, and thus the introduction of vapor samples into fuel cell 106.

A flow apparatus suitable for use in ignition interlock systems is disclosed in, for example, U.S. Pat. No. 5,426,415 to Prachar et al., entitled "Breath Analyzer For Use In Automobile Ignition Locking Systems," which is hereby incorporated by reference herein. In this system, a diaphragm pump is used to divert a portion of a breath sample through a fuel cell sample electrode while exhausting flow from the sample electrode. Flow structures suitable for use in a breathalyzers are described in, for example, U.S. Pat. No. 4,487,055 to Wolf, entitled "Breath Alcohol Testing device," and in U.S. Pat. No. 5,291,898 to Wolf, entitled "Breath Alcohol Device," both of which are incorporated herein by reference. In these systems, a diaphragm draws breath into and from a chamber adjacent a fuel cell sample electrode to control exposure of the fuel cell sample electrode to the breath.

As described above, flow apparatus 104 can be connected to one or more fuel cells 106 to facilitate analysis of a vapor sample. Fuel cell 106 can be any fuel cell that can produce a response to desired compositions. Suitable fuel cells include, for example, PEM fuel cells, phosphoric acid fuel cells, molten carbonate fuel cells and solid oxide fuel cells, as noted above. In some embodiments, fuel cell 106 can be a PEM fuel cell comprising a proton exchange membrane as the electrolyte, such as Nafion®, with catalyst particles in contact with the electrolyte forming the sample electrode and counter electrode. A current collector contacts the electrolyte particles to complete the electrodes. A particular embodiment is described further with respect to the Examples below. In some breathalyzer fuel cells, the separator is formed from sintered or pressed polymer balls, such as polyvinylchloride, to form pores with about 1 to about 25 micron diameters extending through the membrane. A layer of catalyst mixed with conductive carbon and binder is applied to each side of the membrane to form the sample electrode and the counter electrode. The porous framework can be filled with sulfuric acid, phosphoric acid or a mixture thereof to complete the circuit, although other electrolytes can be effectively used.

Suitable analysis instruments include, for example, windows based computers, person digital assistants, and dedicated computer processors, i.e., microprocessor, integrated into a portable analysis apparatus, in which portable digital assistant technology can be incorporated into the apparatus.

Acetone Detection

As will be discussed below, the time response to acetone produces a signature negative curvature when using a fuel cell sensor. This time response indicates that the acetone is reduced at the fuel cell cathode, although the reduction product may be subsequently oxidized at the same electrode. After an initial rise, the signal from an aqueous acetone solution rapidly decreases and then increases to a maximum followed by slow decay. This distinctive short time negative peak from acetone reduction can provide a signal that enables ready estimation of acetone concentrations in alveolar air and discriminate against possible interferents on the breath, such as ethanol and cigarette smoke. The distinctive wave shape for acetone is observable at suitably lower concentrations of acetone of biological relevance. Thus, a breath-based fuel cell sensor enables quantifying breath acetone that is associated with diabetic ketoacidosis and effective management of a ketogenic diet and serves as a screening tool for the diabetic state.

Due to the presence of the negative peak, several approaches can be used to estimate the amount of acetone in a person's breath sample. However, the acetone signal with the negative peak is generally on the same order of magnitude as a "clean" breath signal (breath with no detectable acetone concentration). In contrast, the response of the fuel cell sensor to ethanol and smoke is much stronger than fuel cell response to "clean" breath (or acetone spiked breath) so that a "clean" breath signal generally can be ignored for an ethanol evaluation. In other words, any signal due to "clean" breath does not need to be subtracted from the representative ethanol or smoke signals, and a "clean" breath signal does not need to be subtracted from actual breath samples to evaluate significant ethanol contributions. On the other hand, to determine the presence and amount of acetone on a person's breath, a subject's "clean" breath generally may be taken into consideration in some analysis approaches.

Three different algorithms to estimate the acetone concentration in a person breath are discussed. In the following section, an approach for evaluating a person's breath for a plurality of medically related analytes is discussed. The concentration of acetone in the person's breath provides information on the corresponding blood sugar level(s) and metabolic/diabetic state of the subject. The potential or current is a function of time, and these functions can be considered vectors from a calculational perspective with the discrete time points selected as described below in the context of more general algorithms for multiple analytes.

In a first approach, the fuel cell sensor signal is taken as a linear combination of an acetone signal and a "clean" breath signal. To build a calibration set, a signal vector can be used that has a known amount of acetone ($V_{acetone}$, which is an acetone concentration slightly above the highest level one would ever expect to find on a subject's breath). A signal that is known to not carry acetone ($V_{clean}$) is subtracted from $V_{acetone}$. "Clean" samples can be collected by bubbling clean, compressed air or a healthy person's breath through a water bath at 37° C. (body temperature). Linear combinations of $V_{acetone}$ and $V_{clean}$ are taken to match a real subject's breath ($V_{sample}$) and an appropriate calibration table based on the original concentration of acetone used to collect $V_{acetone}$ is used to determine the acetone concentration. To evaluate the amount of acetone in an individual's breath, the following equations can be used with a non-linear fit using the vectors:

$$C_1 \times V_{acetone} + C_2 \times V_{clean} = V_{lin.\ Combo}, \quad (1)$$

$$\text{Absolute Value of } \Sigma(V_{lin.\ Combo} - V_{sample})_i = \text{Gross Error}, \quad (2)$$

where the minimum Gross Error (GE) gives the best fit result. The summation for calculating the Gross Error involves a summation over different time points. To do the minimization, the values of $C_1$ and $C_2$ can be obtained by minimization for each concentration dependent standard vector $V_{acetone}$ ($C_a$), where $C_a$ is a particular acetone concentration for evaluating the standard potential or current response curve. Then, for each value of the standard concentration, the gross error can be evaluated. The sample concentration can be estimated as the concentration of the standard response curve that leads to the lowest gross error.

Since the most distinctive portion of the acetone response curve is at relatively short times, the calculation can be weighted using a fixed weight vector, $V_{weight}$. For example, the weight vector can have a step function that cuts off the time at a cut off, such as 35 seconds. As another example, $V_{weight}$ can be two from 5 to 15 seconds and one elsewhere. Then the gross error can be generalized to the following:

$$\text{Absolute Value of } \Sigma(V_{weight}(V_{lin.\,Combo} - V_{sample})_i) = \text{Gross Error}, \quad (3)$$

which involves a vector dot product and i indicates a particular time point.

By developing the table of linear combinations of $V_{acetone}$ and $V_{clean}$ ahead of time, a very simple instruction set can be used that would execute quickly on even the very low cost hardware presently available. If the negative acetone spike is not linear with the concentration of acetone the subject's breath is compared with a table of vectors; each vector representing a particular acetone concentration. These vectors can be determined experimentally using the bubbling apparatus described in the Examples below.

In a second approach, the magnitude, i.e., depth, of the negative peak is used directly to estimate the acetone concentration. The negative peak is superimposed on a positive slope from "clean" breath and possibly an oxidation response related to the oxidation of the acetone reduction product. The negative peak depth can be estimated from the position of the negative peak subtracted from an estimate of the positive going contribution. The positive going contribution can be estimated with a line connecting the local maxima on either side of the negative peak.

In principle, the first derivative curve can be used to locate the local extrema, but this can be complicated from noise in the plot that masks the desired local extrema by generating a large number of local maxima and minima. A variety of numerical approaches can be used to identify the desired extrema, which may or may not involve the input regarding windows on the expected location of the extrema. In a representative approach, the end points of the acetone peak are located with a stepwise approach to identify the local extrema, i.e., a local maximum or a local minimum. The extrema, involving two local maximum with a local minimum between them, can be located as time progresses. In particular, the first maxima $V_{M1}$ can be picked as the highest value from an initial time before a significant dip. The negative peak or dip can be identified as a drop of at least about 1% in magnitude from the first maximum. The lowest point $V_{min}$ in the dip can be identified when the curve increases by at least about 1% in magnitude from the previous minimum. Also, the second maximum can be identified by a subsequent drop of 1% in magnitude from the previous maximum.

More specifically, in one embodiment, starting from an initial reading, a tentative maximum potential/current reading and its corresponding time value are stored as one progresses in time with a new maximum replacing a previous tenetative maximum until a present potential/current reading has dropped at least 1% from the previous maximum reading. When the 1% drop is identified, the tentative maximum potential/current reading is then saved with its time as $V_{M1}$, $t_{M1}$, respectively. Then, a going forward tentative minimum and its corresponding time are stored with a new minimum replacing a previous tentative minimum until the potential/current has gone back up by at least about 1% from the previous tentative minimum value. When this point is reached, the tentative minimum potential/current value is stored along with its time as $V_{min}$, $t_{min}$ respectively. Then, a forward going tentative maximum value and corresponding time are stored with a new maximum value replacing a previous tentative maximum value until the current potential/current value has fallen by at least 1% from the previous tentative maximum value. When this point is reaches, the tentative maximum value and corresponding time are stored as $V_{M2}$, $t_{M2}$, respectively.

Once these values are obtained, a line is fit through ($V_{M1}$, $t_{M1}$)–($V_{M2}$, $t_{M2}$) by solving linear equations for m and b:

$$V_{M1} = m \times t_{M1} + b,$$

$$V_{M2} = m \times t_{M2} + b.$$

Then, the depth D of the negative peak is evaluated as $D = V_{min} - (m \times t_{min} + b)$. To obtain the concentration from this value for D, a set of standard values $D_s$ can be evaluated for D using standard acetone solutions at 37° C., $D_s(C_i)$, where $C_i$ are a set of standard concentrations. Either the value of $C_i$ corresponding to $D_s(C_i)$, which is the closest value of $D_s$ to the sample value of D, can be selected as the estimate of the acetone concentration in the person, or a linear or nonlinear extrapolation can be performed between the two closest values of $D_s$ to get a more precise value of acetone concentration if a higher precision is desired.

In a third approach, the area of the negative spike can be evaluated to estimate the acetone calculation. While slightly more involved than the negative peak depth measurement, the area based approach on average should be less sensitive to noise so that it may be slightly more accurate than the peak depth approach. To estimate the negative peak area, the values of $t_{M1}$ and $t_{M2}$ can be used to fix the end points of the peak. The difference is evaluated between the line $V_1 = mt + b$, with m and b determined as described above and $V_i$ where this is a particular potential/current reading along the negative peak. The difference between the sample value $V_i$ and linear $V_1$, i.e., $(V_i - V_1)$, is integrated between the two time values, $t_{M1}$ and $t_{M2}$. The area is the integral of this difference, and the integration can be performed with any standard numerical integration routine, such as the trapezoid rule integration or others known in the art.

The evaluated area can be compared with standard areas evaluated with standard aqueous acetone solutions. Again, the concentration can be estimated by finding the concentration $C_i$ corresponding with the closest standard area $A_i$ to the sample area A. If greater precision is desired, the standard area values can be linearly interpolated to obtain a more accurate estimate of the sample concentration.

Analysis Algorithm

The time dependent response of the fuel cell is dependent on the chemical composition of the sample introduced into a vapor sampling system of the fuel cell sensor, such as those described herein. Thus, if a sample comprises a plurality of volatile organic and/or inorganic compositions that can react at the fuel cell electrode, the time dependent response curve of the fuel cell reflects the overall composition of the vapor sample. The de-convolution of the time dependent response curve can be used then to obtain the amounts of the different volatile organic compositions in the vapor sample. The de-convolution can be based on a linear combination or a non-linear combination of the independent response curves. The de-convolution of the vapor sample is based on standard curves for the individual compositions, which may be normalized.

The use of a fuel cell signal to de-convolute ethanol contributions from cigarette smoke contributions is described further in published U.S. Patent application 2005/0214169A to Leddy et al., entitled "Multicomponent Analysis of Volatile Organic Compositions in Vapor Samples," incorporated herein by reference. Here, the analysis is generalized to provide for medical diagnosis assisted with an analysis of a breath sample. Acetone is a significant composition for a medical evaluation since it is indicative of diabetic individuals and their maintenance of their condition. As noted above, acetone has a characteristic negative peak at relatively short times indicating a reduction reaction.

The procedure for medical evaluation generally involves a significant component related to the selection of analytes for the de-convolution of the potential/current measurements. To be applicable for a large number of individuals, it is useful to include cigarette smoke and ethanol since these compositions may be on the breath of individuals being evaluated for medical conditions and since these compositions generally yield relatively strong signals. Other analytes of interest include, for example, $CO_2$, COS, $NH_3$, $CS_2$, alkanes, benzene derivatives and NO. In general, the analytes for these measurements may not yield signals as strong as an ethanol signal of an intoxicated person or cigarette smoke for a person who has smoked shortly before the measurement. For these samples, the background "clean" breath signal may be relevant. "Clean" samples can be collected by bubbling clean, compressed air or a healthy person's breath through a water bath at 37° C. (body temperature). Then, the clean breath measurements can be included as one of the analytes within the de-convolution of the sample measurement curve. The de-convolution should work even if an analyte has a negative/reduction peak in its response curve, such as acetone.

To perform the analysis, each curve can be converted to a vector by the selection of a specific number of time points. The dimension of each vector, i.e., the number of time points used, can be selected to obtain a desired degree of fitting. The number of time points is selected to yield a desired accuracy of the de-convolution. All of the collected time points can be used in the analysis such that the hardware response time sets the spacing of the time points, although a subset of the time points can be used as desired. Generally, the data are collected until the signal has significantly decayed from its peak value, and in some embodiments the signal is monitored until it has decayed 60 percent from its peak value, in further embodiments 75 percent from its peak value and in additional embodiments 85 percent from its peak value. A person of ordinary skill in the art will recognize that additional ranges for the time cut-off within the explicit ranges are contemplated and are within the present disclosure.

Generally, the degree of fitting does not significantly increase after a certain number of time points are selected. The number of time points may be fixed by the timing of the data collection system and the response time for the analog-to-digital conversion. In general, the time points do not necessarily have to be equally spaced, although certain spacings may be convenient for certain types of numerical analysis. The resulting vector can be written as V with elements $v_n$ for the nth time point recorded.

Each standard vector can normalized to a normalized vector NV for the later de-convolution. Specifically, the normalization is performed according to:

$$\text{The } N\text{th Normalized element in } NV = Nv_n = (v_n - v_{small})/(v_{large} - v_{small}), \quad (1)$$

where $v_{small}$ is the smallest element in V, $v_{large}$ is the largest element in V. Equation (1) ensures that the largest value in NV is 1 and the smallest value is 0. Other normalizations can be used to standardize the peak value, if desired, although the normalization in Eq. (1) has been found in the examples below to yield good results.

A number of normalized curves from known samples can be averaged to get a standard curve $V_{average}$ for a particular analyte, such as acetone, ethanol, cigarette smoke, COS, $CS_2$, NO, clean breath or any other volatile organic and/or inorganic composition. Depending on the magnitude of the other signals in the sensor, it may be useful to include "clean" breath as one of the analytes. The standard vector for analyte "a" from an average of i sample runs can be written as:

$$N\text{th element of the standard vector for analyte } a = V_{average,a} = V_{na} = (Nv_{na1} + Nv_{na2} + \ldots + Nv_{nai})/i \quad (2)$$

where $Nv_{nai}$ is the nth normalized element at $t_n$ for the i-th sample of analyte a. In general, slight variations between vectors $NV_1$ to $NV_i$ distort the values of $V_{average}$, so that the largest value in $V_{average}$ is not necessarily equal to 1, and the smallest value in $V_{average}$ is not necessarily equal to 0. Thus, the average response curve itself can be normalized based on the formula in Eq. 1 to obtain a normalized average or standard curve for a particular analyte, $NV_{average}$.

A linear combination of the vectors $NV_{average,A}$, $NV_{average,B}$, $NV_{average,C}$, etc. can be used to form a vector V that approximates a sample vector. In principle, any number of standard vectors for analytes A, B, C, D, ... can be used. In some embodiments, there are 2 analytes, such as acetone and cigarette smoke, in other embodiments, 3 analytes, in further embodiments 4, in additional embodiments 50 or more, and any number in between. The instrument can use alternative algorithms based on input from the operator. For example, an algorithm can be selected that includes de-convolution involving cigarette smoke if the subject is a smoker or ethanol if the person had a drink in the previous 6 hours or other time threshold. A selection among a few different algorithms can provide improved sensitivity for other analytes, and the instrument generally can be simply programmed to achieve this selection among algorithms.

For two analytes, the equation is as follows:

$$V_{Lin.\ Combo.} = A \times NV_{average,A} + (1-A) \times NV_{average,B}, \text{ where } 0 \leq A \leq 1 \quad (3).$$

For three analytes A, B and C, this equation becomes:

$$V_{Lin.\ Combo.} = A \times NV_{average,A} + B \times NV_{average,B} + (1-A-B) \times NV_{average,C}, \quad (4)$$

where $0 \leq A \leq 1$ and $0 \leq B \leq 1$. Equations for other numbers of analytes can be written based on these examples. In general, there are N-1 unknowns for N analytes. Thus, as long as there are at least N-1 time points, the linear combination (or nonlinear combination) can be fit, although having additional time points presumably leads to a better fit through an over determination of the linear fit.

The new linear combination vector can be normalized according to Eq. 1. Similarly, the sample vector can also be normalized to yield a vector $NV_{unknown}$. Because the two vectors, $NV_{Lin.Combo.}$ and $NV_{unknown}$ are normalized to the same range, the proportions of the signal due to the two analytes, ethanol and cigarette smoke in the example below, the proportions of the two analytes can be evaluated regardless of the absolute magnitude of the response. The calculation at some point involves scaling the linear combination curve to the actual measurement to obtain the absolute quantities of the analyte. This scaling back to the total values can be performed before or after the fitting.

The best fit for the unknowns can be determined using established mathematical techniques. Thus, for Eq. 3, $A_{Best\ Fit}$ is determined, and similarly, for Eq. 4, $A_{Best\ Fit}$ and $B_{BestFit}$ can be determined. For example, the unknown parameters can be obtained by iteration. The sum of the differences between the elements in $NV_{Lin.\ Combo.}$ and $NV_{unknown}$ can be called the "Gross Error" and is defined by the following equation:

$$\text{Gross Error} = \Sigma |Nv_{n,unknown} - Nv_{n,\ Lin.\ Combo.}| \quad (5).$$

Equation (5) results in a fit that weights all time points equally. Other expressions for the gross error can be used, if desired. This fitting to reduce the gross error to obtain the best fit can use standard approaches to automate the process. An initial value can be estimated for the parameters based on known information about the sample. Standard methods for performing the fit are known, such as the Downhill Simplex Method and the Conjugate Gradient Method. These are described further, for example, in Numerical Recipes: The Art of Scientific Computing, W. H. Press et al., (Cambridge University Press, 1986), incorporated herein by reference.

Once the value of $A_{BestFit}$ is known, it can be used to obtain BrAC or other concentrations for other analytes besides ethanol. Similarly, if additional unknown parameters are calculated for other analytes, these can be used to obtain useful concentration information. For a particular parameter, the concentration data can be obtained from the following calculation:

$$\begin{aligned}\text{BrAC or other Concentration value} &= A_{BestFit} \times \\ C_{Calibration} &\times (V_{large,LinCombo} - V_{small,LinCombo}) \times \\ &(V_{large,Unknown} - V_{small,Unknown})\end{aligned} \quad (6).$$

Similar integration based calibrations to obtain areas of peaks or other areas of the time response curve are also possible to obtain concentrations.

$C_{calibration}$ can be obtained from a calculation of the responses of a fuel cell to a known, pure analyte sample. The concentration value for the vapor sample is then divided by the response to yield $C_{calibration}$. The last part of Eq. (6), i.e., $(v_{large,LinCombo} - v_{small,LinCombo}) \times (v_{large,Unknown} - v_{small,Unknown})$, uses the largest and smallest values in vectors $V_{Unknown}$ and $V_{LinCombo}$ and is a scalar ratio between the range of the response to the unknown sample and the range of the linear combination fit. Since the linear combination of the normalized analytes responses are used, this scalar ratio can be used to find the actual response curve for that analyte.

Equations (3) and (4) above are directed to linear combinations of the fuel cell response for the different analytes. However, there may be circumstances in which the analytes interact in the anode such that the response of the fuel cell may be non-linear with respect to the presence of the different analytes. For example, Eq. (3) can be generalized to:

$$V_{Nlin.\ Combo.} = A \times NV_{average,A} + (1-A) \times NV_{average,B} + C \times (NV_{average,A} \times NV_{average,B}). \quad (7)$$

The parameters for the nonlinear fit can be established by obtaining the smallest value of the Gross Error in a similar fashion as the linear parameters were established. The parameters A and (1-A) can similarly be used to evaluate concentrations of the analytes as described above.

EXAMPLES

In performing the measurements herein, the apparatus incorporated a design with a fuel cell as described below. The fuel cell is placed within the apparatus to provide regulated breath flow to the anode of the fuel cell. The fuel cell output voltage was converted to a digital signal with an A/D converter for analysis by a computer. The analysis was performed through an iteration using 0.001 increments in the parameters over the range of possible values. This approach is straightforward to implement with computationally limited processors.

The fuel cells used in the test devices are essentially described in U.S. Pat. No. 5,928,804 to Leddy et al., entitled, "Fuel Cells Incorporating Magnetic Composites Having Distinct Flux Properties," which is hereby incorporated by reference, except that the fuel cells did not contain magnetic composites. These fuel cells are proton exchange membrane fuel cells with Nafion® perfluoronated, sulfonic acid polymer used as the electrolyte/separator. The ionomer Nafion® has superior ionic conductivity. Platinum coated carbon black particles (20 weight percent platinum) were used as the catalysts. The catalyst particles are formed by mixing Pt from Alfa Aesar with carbon black (XC-72 from E-Tek) and mixing vigorously with a drill. The fuel cells were prepared with catalytic ink preparation and application procedures, Nafion® membrane pretreatments, and hot press lamination techniques. Specifically, a catalytic ink is mixed from platinum, carbon black, water, ethanol and isopropyl alcohol. This combination is mixed thoroughly. This solution is applied to carbon cloth or carbon paper (Toray paper) by painting with a brush or spraying with an air brush. Suitable carbon paper or carbon cloth are available from Aldrich Chemical or E-Tek. Solubilized Nafion® (Ion Power or Aldrich) is then sprayed over the dry ink that has already been supplied to the electrode(s). The two counter electrodes are formed equivalently. A Nafion® membrane (Aldrich or Ion Power) is sandwiched between the two electrodes and hot pressed at about 130 degrees C. under about 0.1 metric tons per square centimeter. The membrane electrode assembly (MEA) is allowed to cool while under pressure. Once cooled to about 50 degrees C., the MEA can be removed from the press for use.

The catalyst/separator interface has the bulk of the catalyst sites available to volatile reactive compositions in the vapor sample, in comparison with commercial breathalyzer fuel cells. The fuel cells were circular with diameters of about 1.5 centimeters and are mounted in cartridges for easy exchange within the testing apparatus. Due to their construction and corresponding high general sensitivity, the fuel cells have unique time response curves with respect to volatile compositions of interest. In particular, commercial breathalyzer fuel cells tend to be much more sensitive to ethanol than to other types of volatile organics.

The test apparatus provided for the introduction of various breath samples under specified conditions into the fuel cell. Data were collected at 10 Hz, i.e., 10 points per second for 1 to 100 seconds for a total of 990 time points. For the examples below directed to the separation of measurements of ethanol and cigarette smoke, the cut off for the time was not significant after 30 seconds. Some testing was performed with standard solutions, while other testing was performed with actual human breath samples. To produce a breath-based test sample, human subjects blew into the device for ten seconds. The first six seconds of the sample were allowed to bypass the fuel cell. The last four seconds of a run come from deeper within the subject's lungs. Thus, last four seconds of the breath is sampled for flow into the fuel cell. A pump with a valve system controls the flow to the fuel cell. A computer records the fuel cell voltage multiplied by 10,000 as a function of time. The fuel cell temperature was 25° C. for all samples. To control the conditions for the test, the tests were performing a in a controlled environment chamber.

Example 1

Evaluation of Reproducibility

This example is directed to the evaluation of reproducibility of the time response curves for different fuel cells assembled as described herein.

Three fuel cell test devices were constructed as described above. "Breath" samples were produced and introduced into each of the fuel cell test devices. The "breath" samples were generated using a Toxitest Breath Alcohol Simulator containing a 0.05 BAC standard solution. The solution was formed with a mixture of ethanol and water to simulate a blood sample and heated to 37° C. to simulate body temperature. Breath was bubbled through the solution to simulate a breath sample. A known quantity of the "breath" sample was introduced into the fuel cell of each fuel cell test device.

Figure 3:
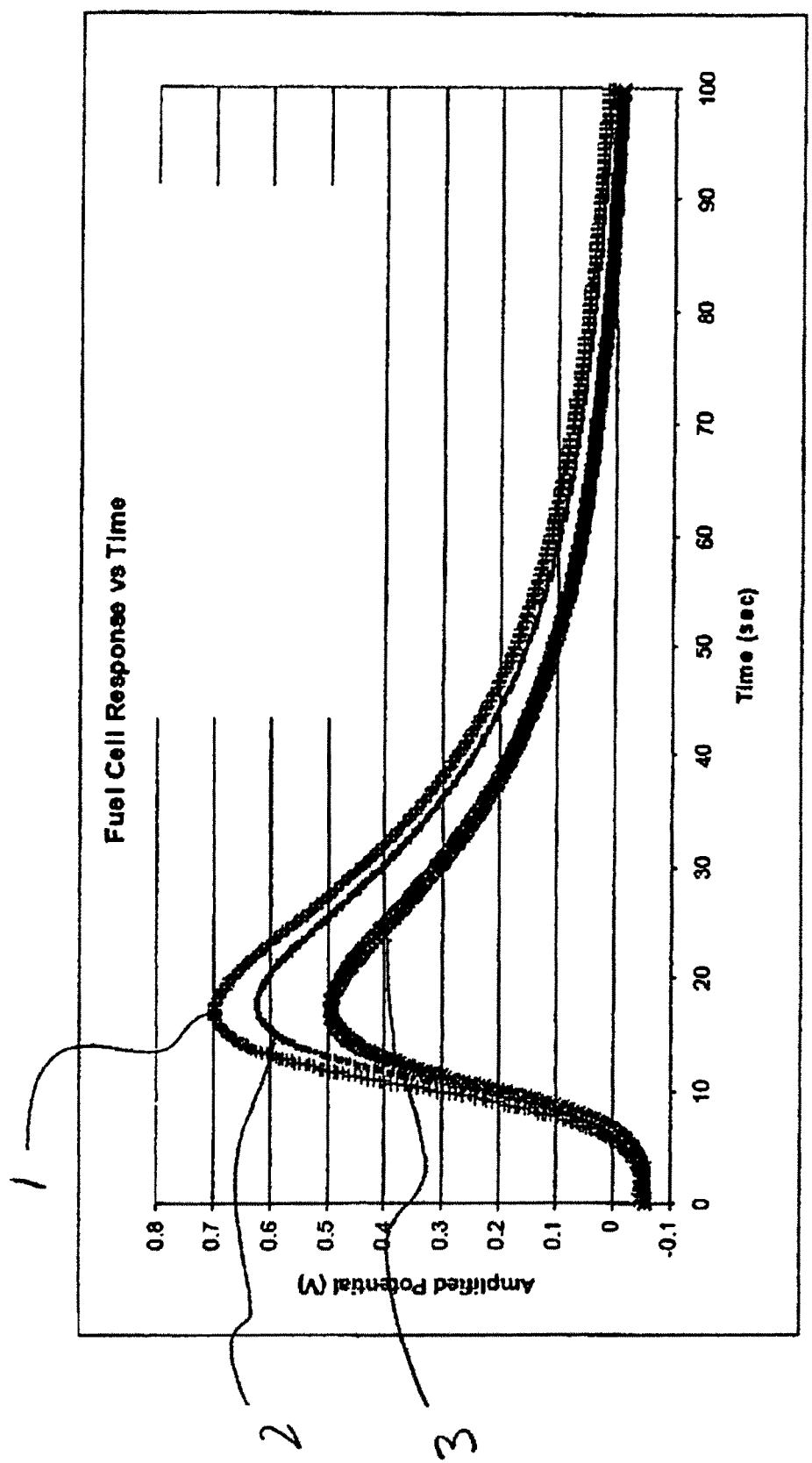
FIG. 3 is a plot of fuel cell response as a function of time for three fuel cells using a standard ethanol sample to compare the results of different fuel cells assembled into the apparatus for evaluating vapor samples.

As depicted in FIG. 3, the shape of the amplified potential v. time curve is similar for all three fuel cells. However, the magnitude of the three curves are different, with fuel cell 1 having the largest magnitude, followed by fuel cell 2 and fuel cell 3, respectively. The magnitude of each curve is different because of the inexact nature of catalyst application during construction. In other words, one particular fuel cell may have more catalyst than another fuel cell, which appears to affect the magnitude of the response curve but not the general shape of the response curve. Since the shapes of the curves are the same, the usefulness of the fuel cells for the detection of different volatile organic compositions should not depend on the magnitude of the available catalyst and differences in catalyst loading is at least in part corrected by the normalization.

Example 2

Cigarette Smoke Detection

This example is directed to detection of cigarette smoke in breath as a function of time from inhaling smoke from the cigarette.

Figure 4:
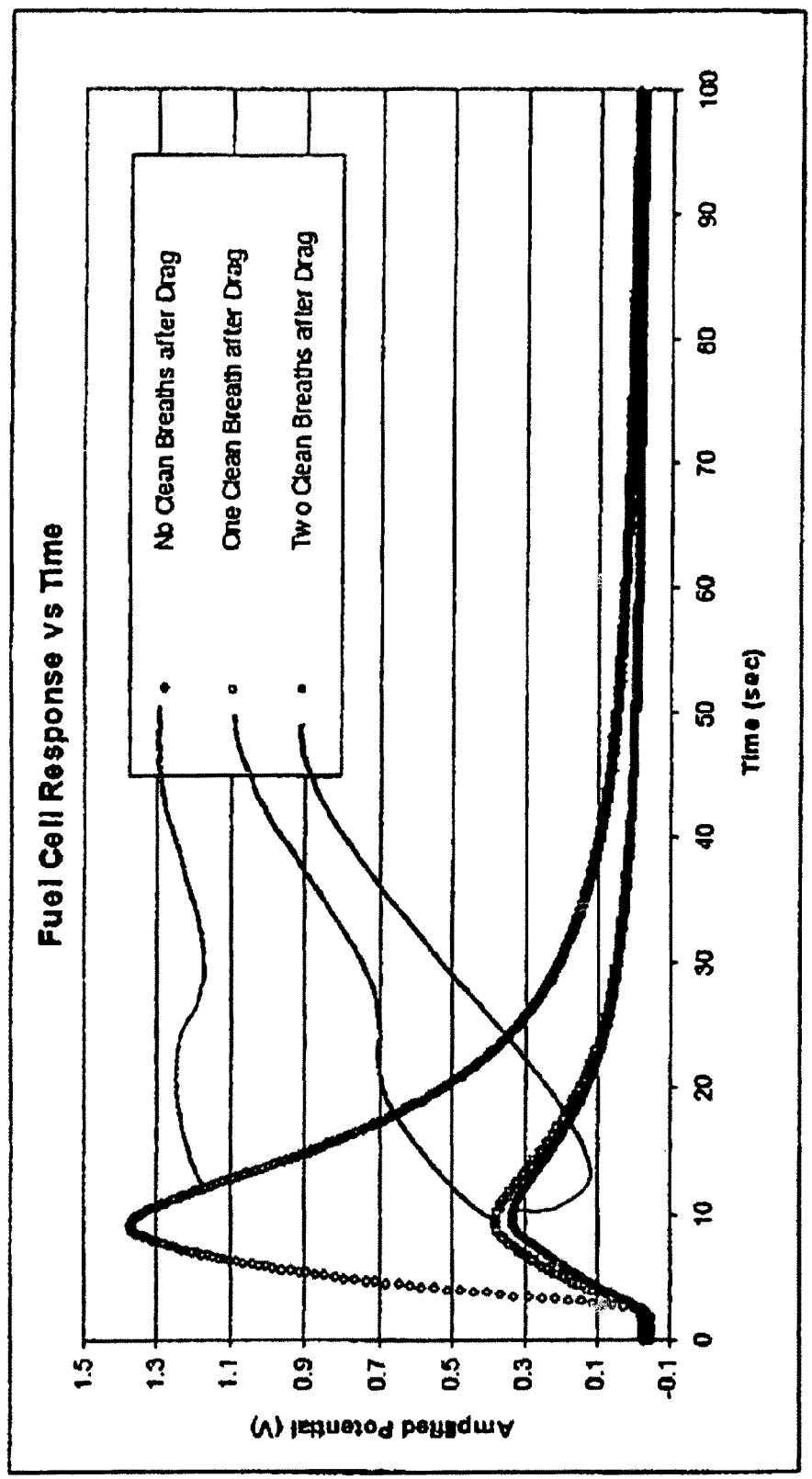
FIG. 4 is a plot of fuel cell response as a function of time for breath samples taken from a person after taking a drag on a cigarette, after taking one clean breath after a drag on a cigarette, and after two clean breaths following a drag on a cigarette.

Breath samples containing cigarette smoke from a single individual were introduced into a fuel cell test device as described above. The shape of the amplified potential v. time curve for each breath sample was similar, however, the magnitude of the curve decreased over time as the number of "clean" breaths after inhalation of the cigarette increased. In other words, the magnitude of the response to cigarette smoke is dependent on time. Referring to FIG. 4, the curve with the largest magnitude was from a breath sample taken after no clean breaths, while the curve with the smallest magnitude was from a breath sample taken after two clean breaths after a drag. The shape of the amplified potential v. time curve has been found to be consistent for at least one hour after a cigarette has been inhaled. Additionally, the shape of the curve has been consistent for different brands of cigarettes. Thus, the approaches described herein can be generally effective for the detection of cigarette smoke on human breath.

Example 3

"Clean" Breath Samples

This example is directed to the comparison of the breath of a non-smoker with the breath of a smoker after a 24 hour period without smoking.

Figure 5:
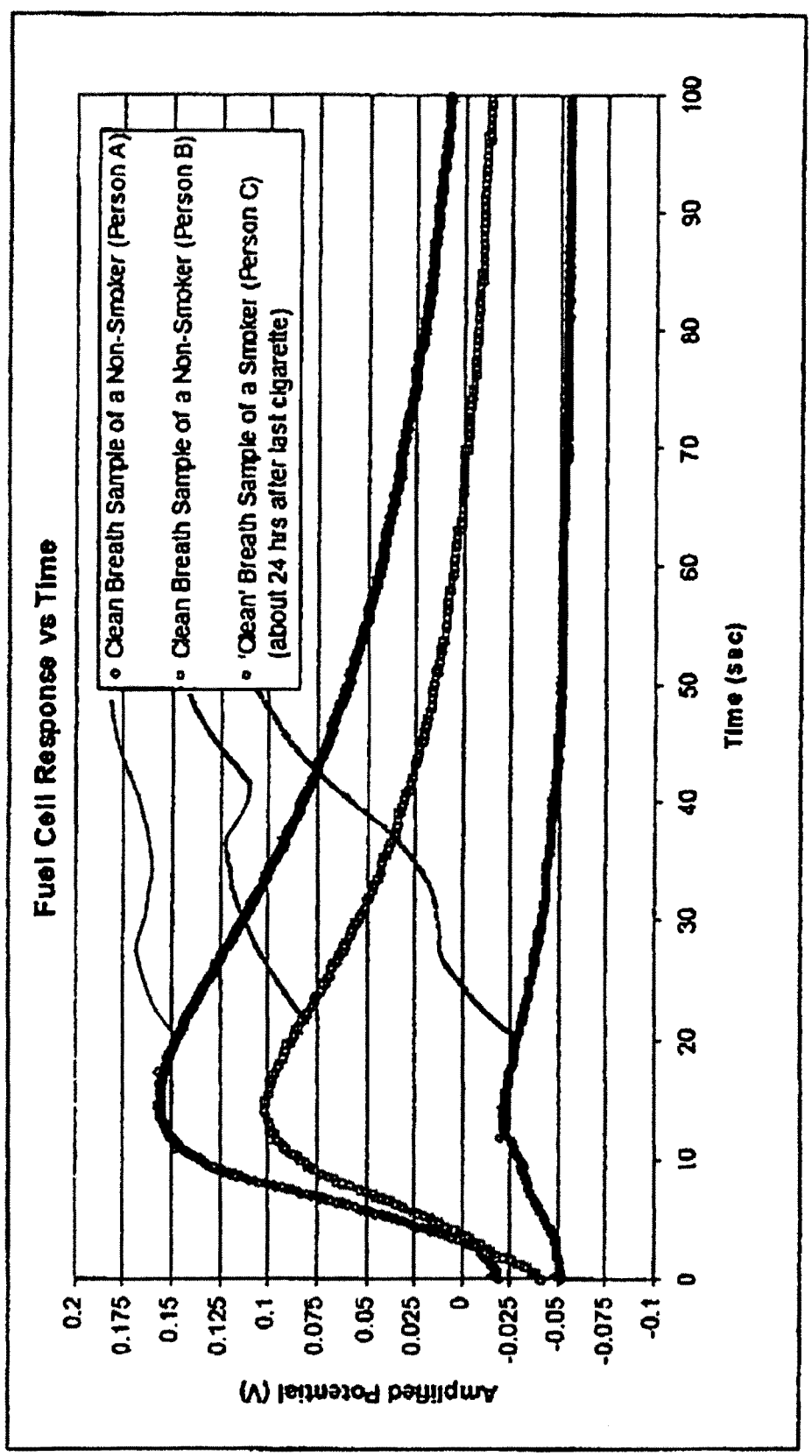
FIG. 5 is a plot of fuel cell response for the breath of two non-smokers and one smoker with at least 24 hours since having smoked their last cigarette.

Clean breath samples were introduced from different individuals into a fuel cell test device as described above. Two of the individuals who provided breath samples were non-smokers, while the other individual was a smoker who had not inhaled a cigarette for about 24 hours prior to giving the breath sample. As depicted in the FIG. 5, the shape of the amplified potential v. time curve for all three individuals is similar. Thus, significant voltage, or response, is not detected by individuals who have "clean" breath.

Example 4

Distinguishing Ethanol and Cigarette Smoke

This example demonstrates the ability to distinguish ethanol and cigarette smoke on the breath of a subject.

Breath samples from regular smokers who had been consuming alcohol were introduced into a fuel cell test device as described above. As depicted in the figures below, the total amplified potential v. time curve can be approximated as a linear combination of the separate responses to cigarette smoke and ethanol components. based on the analysis using Equations (3) and (5) above. The linear combination fit was conducted for data taken between 1 and 100 seconds, using a data sampling rate of 10 Hz.

Figure 6:
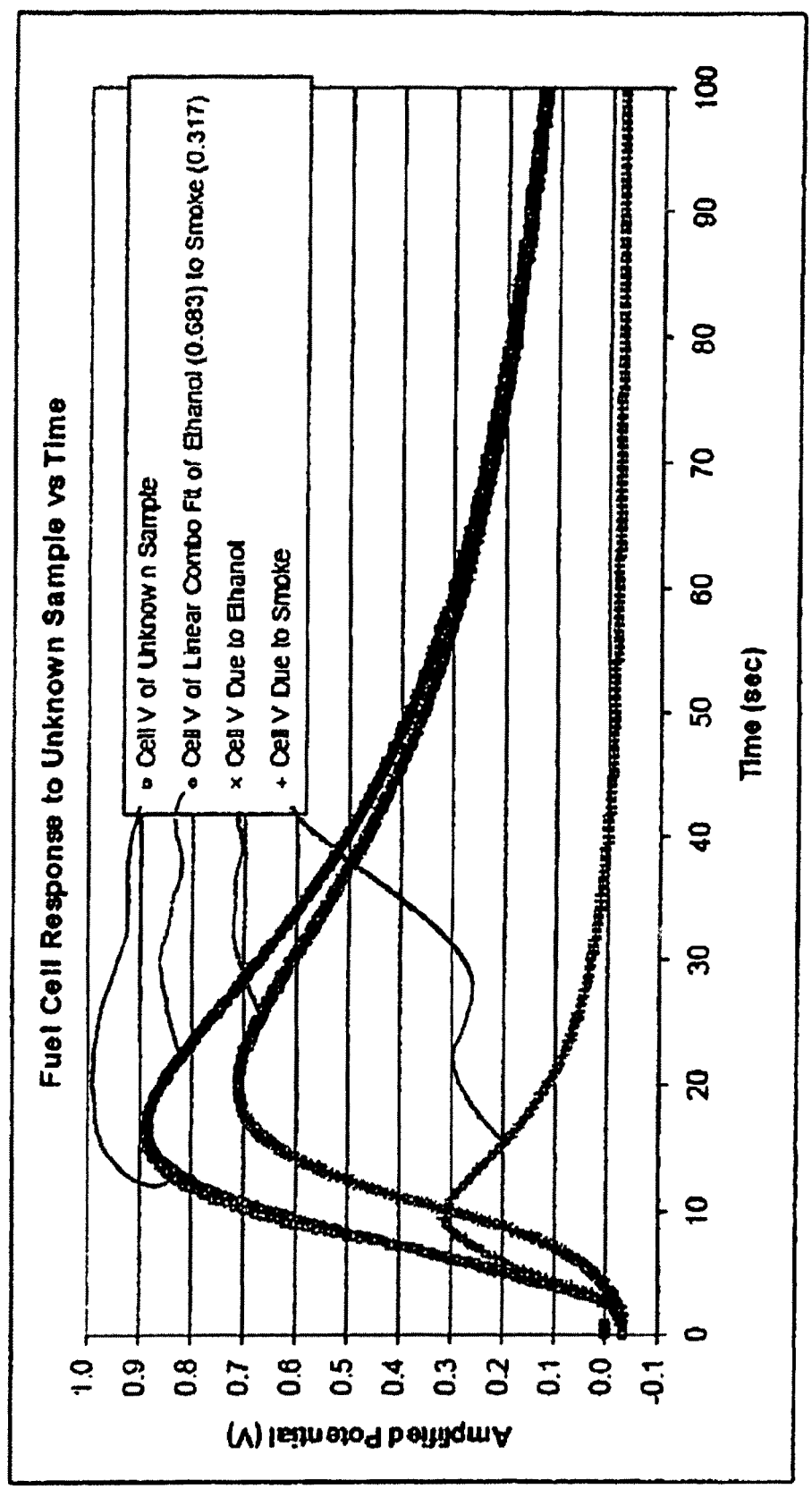
FIG. 6 is a plot of fuel cell as a function of time after an unknown sample from a smoker with ethanol on their breath, plotted along with a fit to ethanol and smoke from standard curves and the resulting curve fit to the unknown sample.
Figure 7:
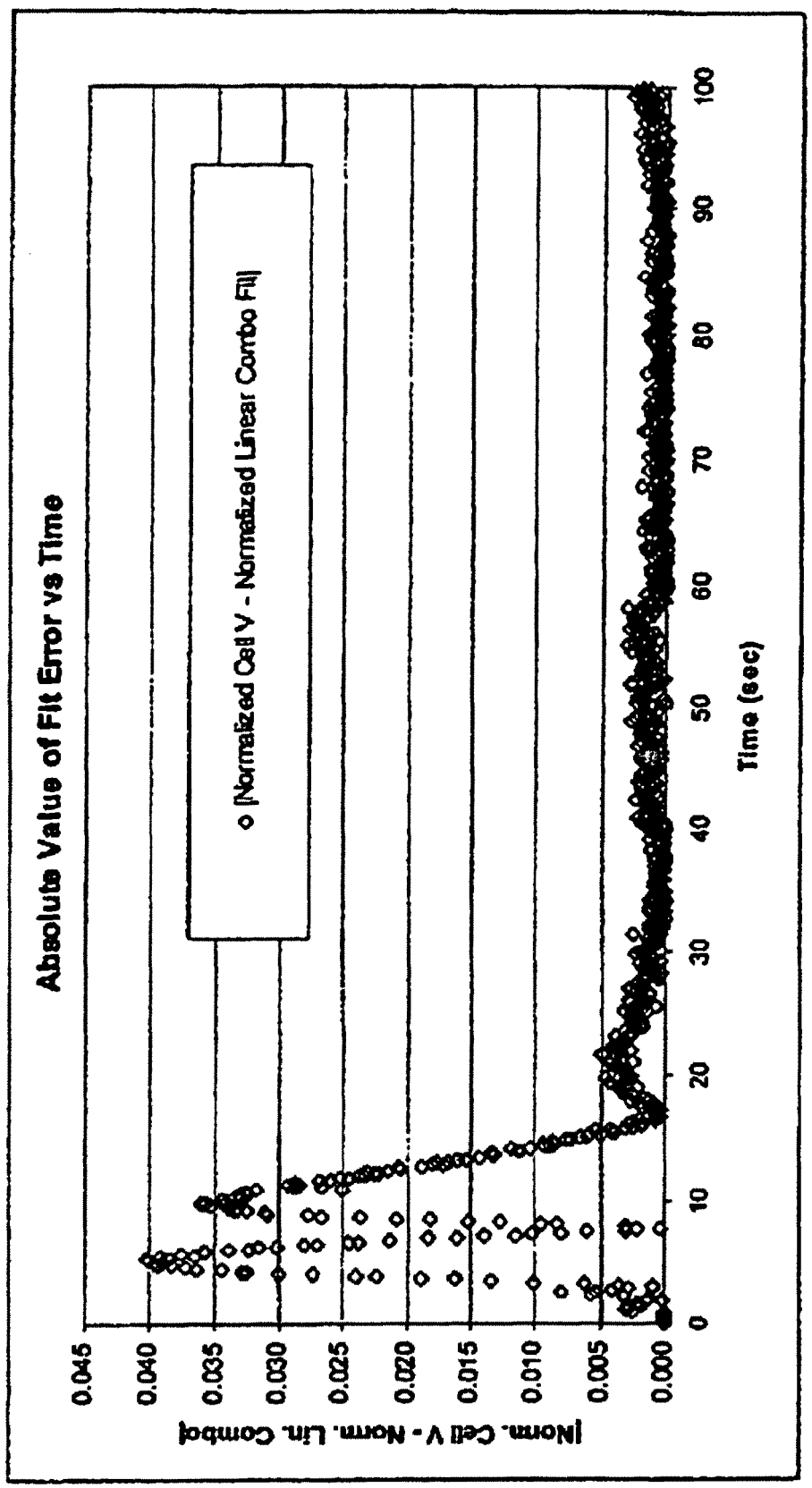
FIG. 7 is a plot of the absolute value of the unknown sample response minus the normalized recombination fit for the data in FIG. 6.
Figure 8:
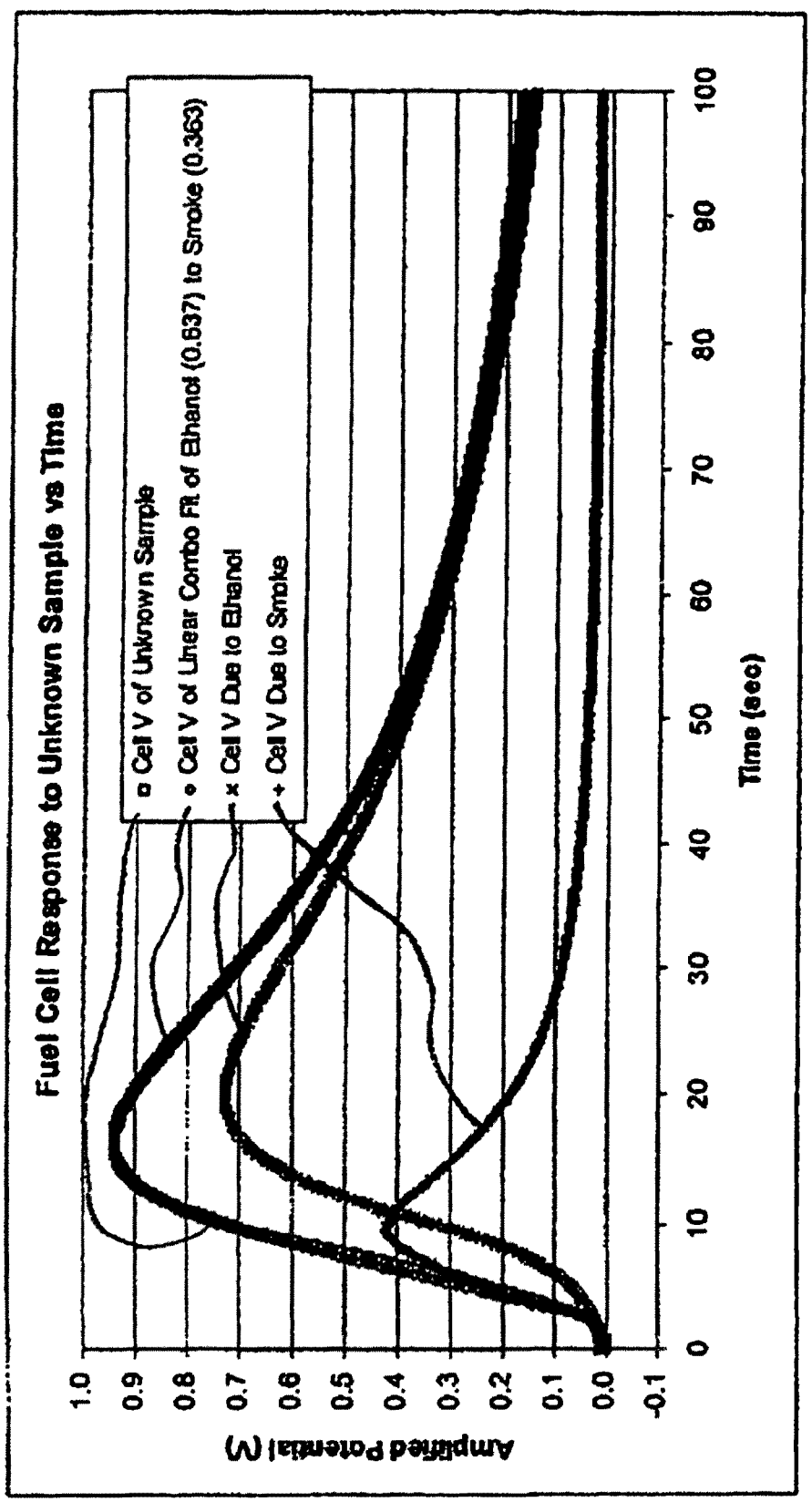
FIG. 8 is a plot of fuel cell as a function of time after a second unknown sample from a smoker with ethanol on their breath, plotted along with a fit to ethanol and smoke from standard curves and the resulting curve fit to the second unknown sample.
Figure 9:
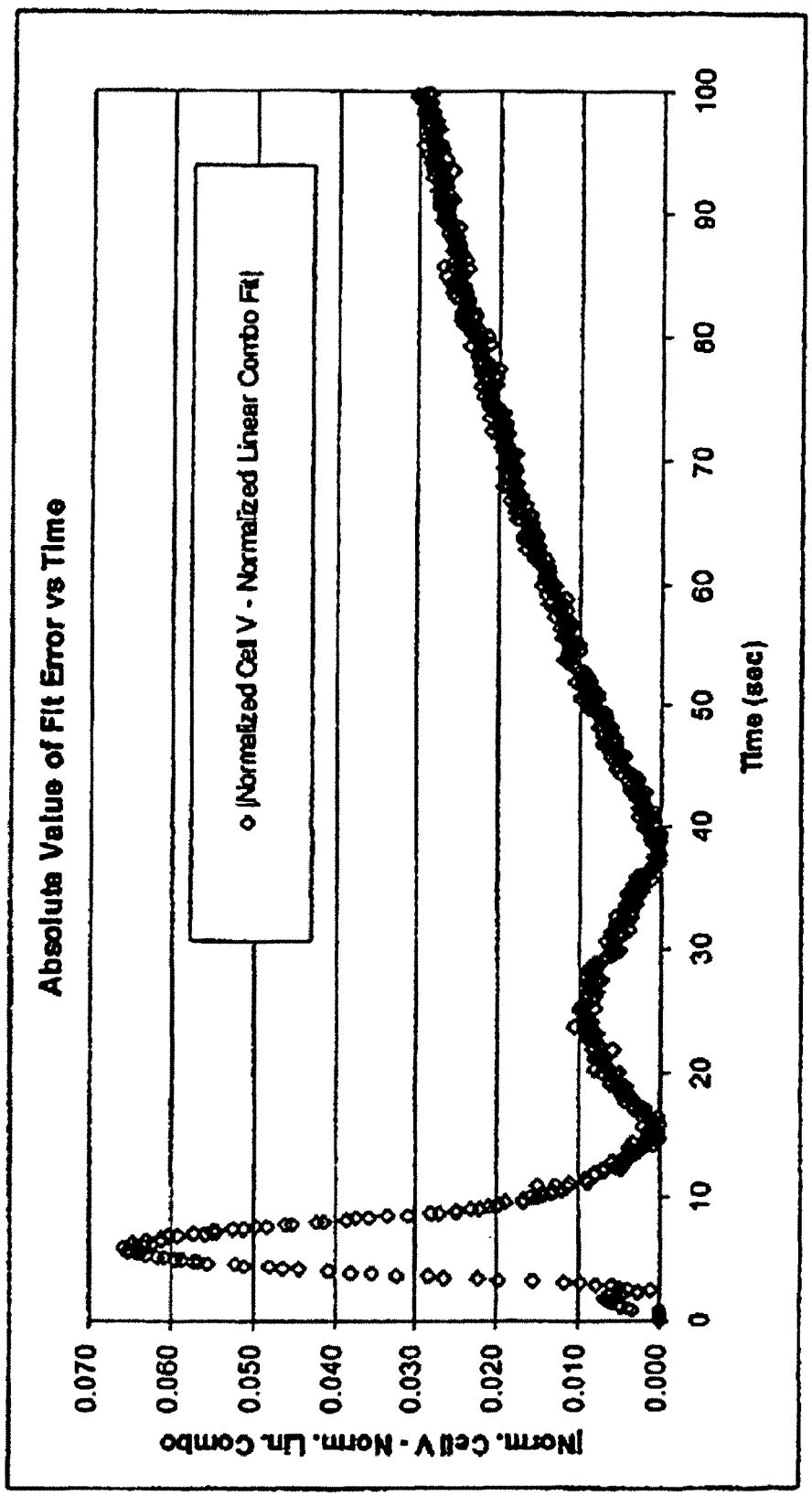
FIG. 9 is a plot of the absolute value of the second unknown sample response minus the normalized recombination fit for the data in FIG. 8.

Results from a first sample are depicted in FIG. 6. The curve was de-convoluted to obtain the contributions from the cigarette smoke and the ethanol, with the ethanol contribution having a larger magnitude and reaching a peak maximum at a significantly later time. A curve is also plotted of the ethanol and cigarette smoke linearly recombined. The linearly recombined curve is very close to the curve of an unknown sample. FIG. 7 is a graph of the absolute value of the normalized response to the unknown sample minus the normalized linear combination fit for the data depicted in FIG. 6. The sum of these errors yields the total gross error, which in this example, is 3.798. The time dependent response of the fuel cell from a second sample is depicted in FIG. 8 along with the de-convoluted ethanol and cigarette smoke responses and the linear fit curve. FIG. 9 is a graph of the absolute value of the normalized response to the unknown sample minus the normalized linear combination fit for the data depicted in FIG. 8. In this example, the gross error is 15.316. These are acceptable errors for this analysis.

This example illustrates that the fuel cell test device can be used to identify multiple organic components in a sample. Additionally, the data presented below in Table 2 represents results from 10 typical samples. The results were produced using the fuel cell device described above. The results in Table 2 indicate that the fuel cell test devices, along with the equations described above, can accurately determine the BrAC of an individual who is consuming alcohol and smoking cigarettes. Thus, the fuel cell test devices can accurately determine the presence and relative amounts of multiple organic compounds in a sample. The coefficient C in Table 2 is another notation for the parameter A from Eq. 3 for these particular analytes.

TABLE 2

Test Results of Ten (10) Typical Samples

| # Clean Breaths After Cigarette | Ethanol Consumed | C | BrAC from Fit | GE |
|---|---|---|---|---|
| Person X (Male) | | | | |
| 0 | 2 oz. in ~43 min. | 0.117 | 0.05 | 12.564 |
| 1 | 2.5 oz. in ~57 min | 0.299 | 0.06 | 6.022 |
| 2 | 3 oz. in ~73 min | 0.468 | 0.06 | 3.831 |
| 4 | 3 oz. in ~96 min | 0.632 | 0.07 | 5.771 |
| >100 (~10 min after last draw) | 3 oz. in ~165 min | 0.641 | 0.06 | 8.141 |

TABLE 2-continued

Test Results of Ten (10) Typical Samples

| # Clean Breaths After Cigarette | Ethanol Consumed | C | BrAC from Fit | GE |
|---|---|---|---|---|
| Person Y (Female) | | | | |
| 0 | 1.5 oz. in ~29 min | 0.130 | 0.05 | 10.063 |
| 1 | 2 oz. in ~48 min | 0.543 | 0.08 | 5.684 |
| 2 | 2.5 oz. in ~61 min | 0.637 | 0.08 | 15.316 |
| 4 | 3 oz. in ~92 min | 0.683 | 0.08 | 3.798 |
| >300 (~30 min after last draw) | 3 oz. in ~160 min | 0.770 | 0.08 | 11.290 |

Example 5

Clean Breath Sample

This example demonstrates the fuel cell response to a "clean" breath sample from a healthy individual. In determining the presence and amount of acetone on a person's breath, a subject's "clean" breath generally is taken into consideration.

Figure 10:
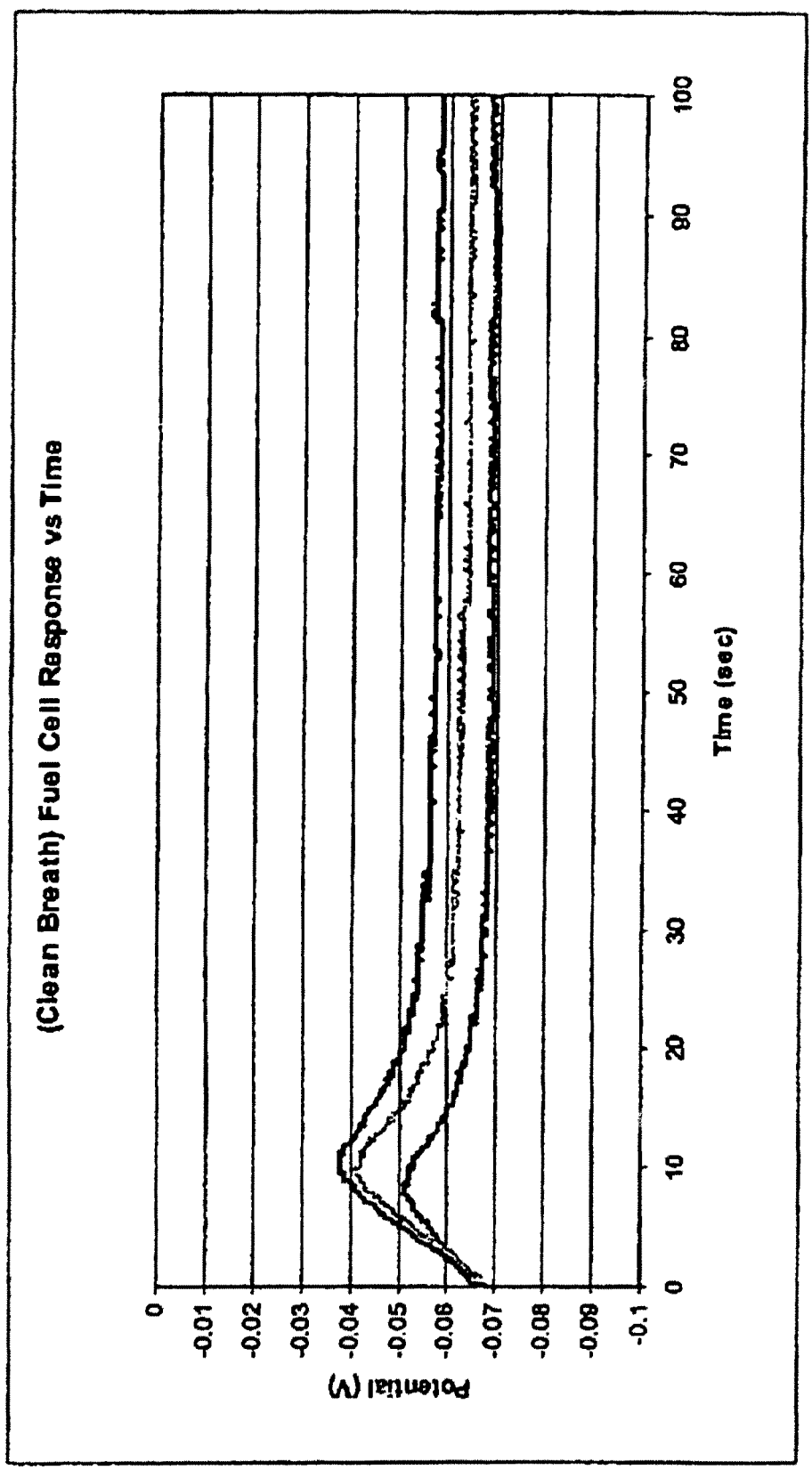
FIG. 10 is a plot of fuel cell response as a function of time for a "clean" breath sample from a healthy individual who had eaten roughly two hours prior to providing the breath samples.

Referring to FIG. 10, the fuel cell response to three "clean" breath samples from a healthy individual is depicted. The individual was a twenty-six year old male (non-smoker, had not been drinking) who had eaten roughly two hours prior to providing the breath samples. The three response curves have a similar shape to each other although they differ in magnitude from each other.

Example 6

Acetone Measurements

This example is directed to the evaluation of the time response curves for different acetone concentrations.

Figure 11:
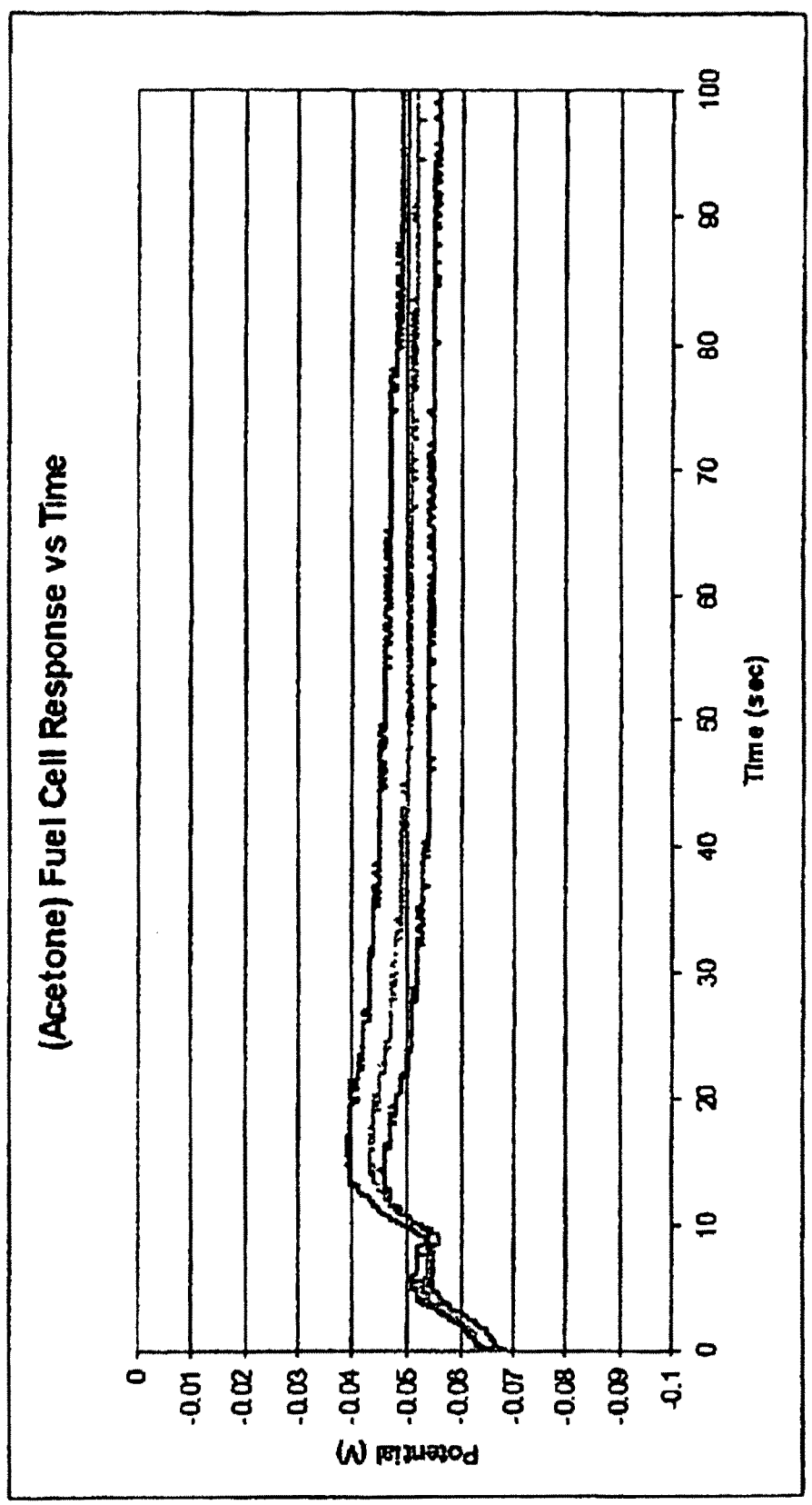
FIG. 11 is a plot of fuel cell response as a function of time for a fuel cell using a 27 mM standard acetone sample.
Figure 12:
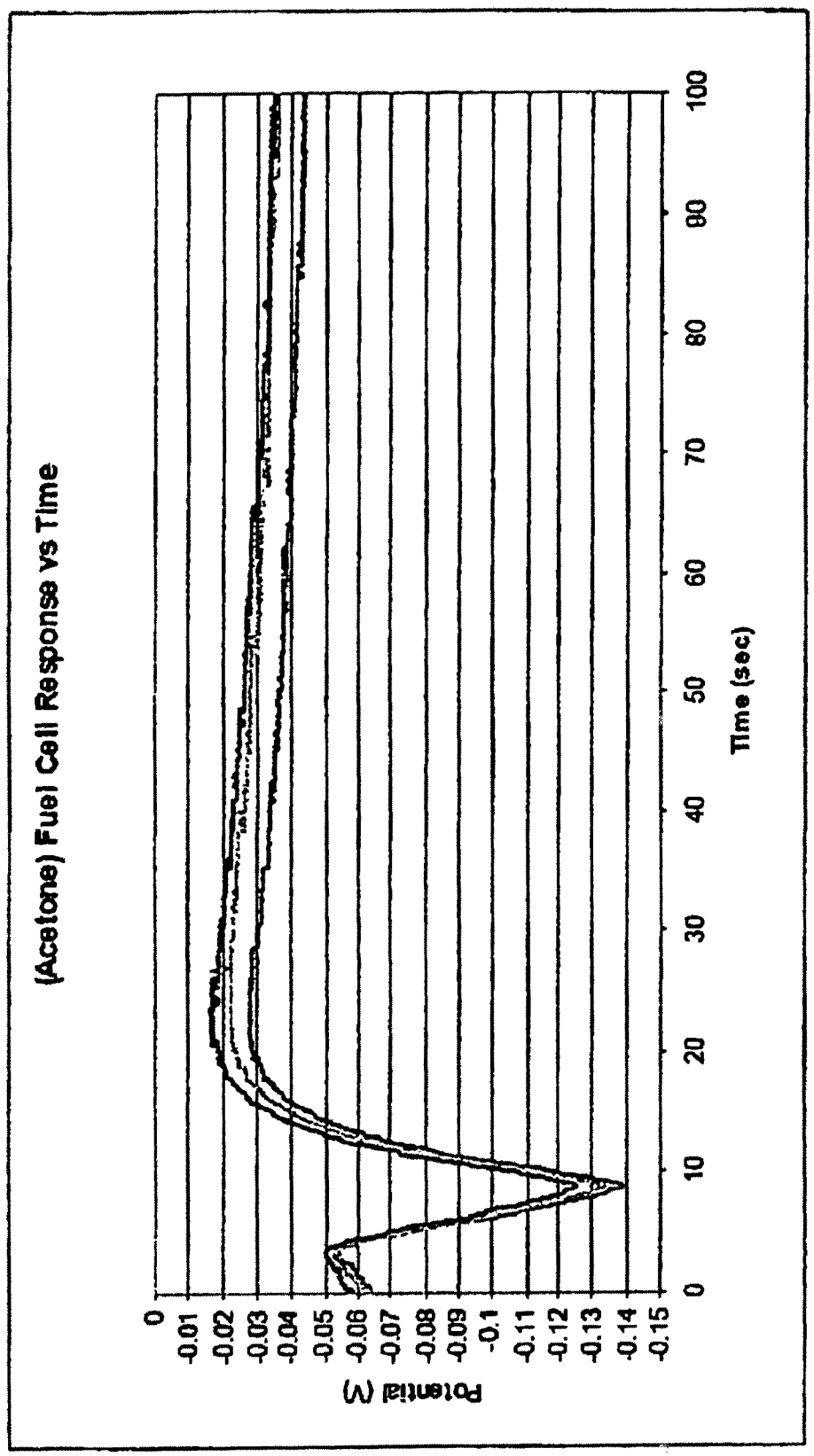
FIG. 12 is a plot of fuel cell response as a function of time for a fuel cell using a 140 mM standard acetone sample.

A fuel cell was constructed as described above. The acetone samples were generated by bubbling air through an acetone solution heated to 37° C. to simulate body temperature using a concentration of acetone in the bath of 27 mM or 140 mM (1 mL and 5 mL of acetone diluted with 500 mL of de-ionized water, respectively). The time response curves of the fuel cell are depicted for three separate samples at each of the two concentrations in FIG. 11 for 27 mM and in FIG. 12 for 140 mM. The curves indicate good reproducibility.

This example illustrates the unusual shape of the curve with the negative component enabling identification of the acetone present in a vapor sample. While the acetone signal is generally smaller with 27 mM acetone relative to the curve for 140 mM acetone, the signal is still characteristic of acetone with the negative component to the response. The negative component indicates that the acetone is undergoing a reduction reaction, although the resulting reduction product may be subsequently oxidized within the fuel cell. Nevertheless, the distinctive negative peak can be used to analyze the breath of a person with respect to detecting the presence and concentration of acetone in a person's breath. The appropriate analytical techniques based on these results are presented above. In particular, average curves from the results in FIGS. 11 and 12 can be used to obtain standard results for these particular concentrations for use in the analyses above.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein.

What is claimed is:

1. A method for an estimation of acetone concentration in a person's breath, the method comprising:
    fitting a sample time response curve of a sample-evaluation fuel cell wherein a sample electrode of the fuel cell is exposed to a breath sample and a counter electrode of the fuel cell is exposed to $O_2$,
    wherein the fitting is performed through the de-convolution of the sample time response curve in comparison of the sample time response curve with the time response curve of standard aqueous acetone solutions,
    wherein standard acetone aqueous solution response curves are compared with the sample response curve to obtain the estimation of acetone concentration in the person's breath, and
    wherein a weighting vector is used to weight different time regions differently.

2. The method of claim 1 further comprising using the fitting to evaluate at least one other volatile organic composition within the breath sample.

3. The method of claim 1 wherein the estimation is performed with a portable breathalyzer comprising the sample-evaluation fuel cell and a microprocessor.

4. A method for evaluating an insulin state of a person comprising:
    estimating the concentration of acetone in the person's blood stream from an estimate of acetone concentration within the breath sample obtained using the method of claim 1;
    correlating the concentration of acetone with a concentration of 3HB; and
    correlating the concentration of 3HB with the insulin state of the person.

5. A method for an estimation of acetone concentration in a person's breath, the method comprising:
    fitting a sample time response curve of a sample-evaluation fuel cell wherein a sample electrode of the fuel cell is exposed to a breath sample and a counter electrode of the fuel cell is exposed to $O_2$,
    wherein the fitting is performed through the de-convolution of the sample time response curve in comparison of the sample time response curve with the time response curve of standard aqueous acetone solutions,
    wherein the sample time response curve comprises a negative peak, a depth of the negative peak being used in the estimation of acetone concentration in an individual's breath by comparing the depth of the negative peak with standard depths evaluated with standard aqueous acetone solutions.

6. The method of claim 5 further comprising using the fitting to evaluate at least one other volatile organic composition within the breath sample.

7. The method of claim 5 wherein the estimation is performed with a portable breathalyzer comprising the sample-evaluation fuel cell and a microprocessor.

8. A method for evaluating an insulin state of a person comprising:
    estimating the concentration of acetone in the person's blood stream from an estimate of acetone concentration within the breath sample obtained using the method of claim 5;

correlating the concentration of acetone with a concentration of 3HB; and correlating the concentration of 3HB with the insulin state of the person.

9. A method for an estimation of acetone concentration in a person's breath, the method comprising:

fitting a sample time response curve of a sample-evaluation fuel cell wherein a sample electrode of the fuel cell is exposed to a breath sample and a counter electrode of the fuel cell is exposed to $O_2$, wherein the fitting is performed through the de-convolution of the sample time response curve in comparison of the sample time response curve with the time response curve of standard aqueous acetone solutions, wherein the sample time response curve comprises a negative peak, an area of the negative peak being used in the estimation of acetone concentration in an individual's breath by comparing the area of the negative peak with standard areas evaluated with standard aqueous acetone solutions.

10. The method of claim 9 further comprising using the fitting to evaluate at least one other volatile organic composition within the breath sample.

11. The method of claim 9 wherein the estimation is performed with a portable breathalyzer comprising the sample-evaluation fuel cell and a microprocessor.

12. A method for evaluating an insulin state of a person comprising:

estimating the concentration of acetone in the person's blood stream from an estimate of acetone concentration within the breath sample obtained using the method of claim 9;

correlating the concentration of acetone with a concentration of 3HB; and correlating the concentration of 3HB with the insulin state of the person.

\* \* \* \* \*